(12) United States Patent
Park et al.

(10) Patent No.: US 8,003,349 B2
(45) Date of Patent: Aug. 23, 2011

(54) YLMPO1 GENE DERIVED FROM YARROWIA LIPOLYTICA AND A PROCESS FOR PREPARING A GLYCOPROTEIN NOT BEING MANNOSYLPHOSPHORYLATED BY USING A MUTATED YARROWIA LIPOLYTICA IN WHICH YLMPO1 GENE IS DISRUPTED

(75) Inventors: Jeong-Nam Park, Daejeon (KR);
Yunkyoung Song, Daejeon (KR);
Jeong-Yoon Kim, Daejeon (KR);
Doo-Byoung Oh, Daejeon (KR); Hyun Ah Kang, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/598,887

(22) PCT Filed: Nov. 30, 2007

(86) PCT No.: PCT/KR2007/006164
§ 371 (c)(1),
(2), (4) Date: Apr. 15, 2010

(87) PCT Pub. No.: WO2008/136564
PCT Pub. Date: Nov. 13, 2008

(65) Prior Publication Data
US 2010/0227362 A1    Sep. 9, 2010

(30) Foreign Application Priority Data

May 4, 2007    (KR) .................. 10-2007-0043806
Jun. 13, 2007   (KR) .................. 10-2007-0057635

(51) Int. Cl.
*C12P 21/06*    (2006.01)
*C12N 9/12*    (2006.01)
*C12N 1/00*    (2006.01)
*C07H 21/04*    (2006.01)

(52) U.S. Cl. .................. 435/69.1; 435/193; 435/254.2; 536/23.2

(58) Field of Classification Search .................. None
See application file for complete search history.

(56) References Cited

U.S. PATENT DOCUMENTS
2006/0160179 A1    7/2006  Bobrowicz et al.

OTHER PUBLICATIONS

Uniport, Accession No. Q6C7Z5 (2004).*
Genebank, accession No. CR382130_31/c (2004).*
Dujon et al. Genome evolution in yeast. Nature, vol. 430, pp. 35-44 (2004).*

Tetsuji, O., et al., "Cloning Analysis of the *MNN4* gene required for phosphorylation of *N*-linked oligosaccharides in *Saccharomyces cerevisiae*," Glycobiology 6(8):805-10, Oxford University Press, United Kingdom (1996).

Boisramé, A., et al., "Interaction of Kar2p and S1s1p is Required for Efficient Co-translation Translocation of Secreted Proteins in the Yeast *Yarrowia lipolytica*," The Journal of Biological Chemistry 273(47):30903-08, The American Society for Biochemistry and Molecular Biology, Inc., United States (1998).

Nakayama, K.-I., et al., "The involvement of *mnn4* and *mnn6* mutations in mannosylphosphorylation of *O*-linked oligosaccharide in yeast *Saccharomyces cerevisiae*," Biochimica et Biophysica Acta 1425:255-62; Elsevier Science B.V., United Kingdom (1998).

Jigami, Y. & Odani, T., "Mannosylphosphate transfer to yeast mannan," Biochimica et Biophysica Acta 1426:335-45, Elsevier Science B.V., United Kingdom (1999).

Conde, R., et al., "Screening for new yeast mutants affected in mannosylphosphorylation of cell wall mannoproteins," Yeast 20:1189-1211, John Wiley & Sons, Ltd., United States (2003).

Jaafar, L., et al., "Isolation of the *MNN9* gene of *Yarrowia lipolytica* (*YIMNN9*) and phenotype analysis of a mutant *ylmnn9* Δ strain," Yeast 20:633-44, John Wiley & Sons, Ltd., United States (2003).

Dujon, B., et al., "Genome evolution in yeasts," Nature 430, Supplementary Information, 53 pages, Nature Publishing Group, United States (2004).

Hobson, R.P., et al., "Loss of Cell Wall Mannosylphosphate in *Candida albicans* Does Not Influence Macrophage Recognition," The Journal of Biological Chemistry 279(38):39628-35, The American Society for Biochemistry and Molecular Biology, Inc., United States (2004).

Madzak, C., et al., "Heterologous protein expression and secretion in the non-conventional yeast *Yarrowia lipolytica*: a review," Journal of Biotechnology 109:63-81, Elsevier B.V., United Kingdom (2004).

International Search Report, including the Written Opinion of the International Searching Authority, for International Application No. PCT/KR2007/006164, Korean Intellectual Property Office, Daejeon, Republic of Korea, mailed Mar. 14, 2008.

International Preliminary Report on Patentability for International Application No. PCT/KR2007/006164; The International Bureau of WIPO, Geneva, Switzerland, issued Nov. 10, 2009.

* cited by examiner

Primary Examiner — Nashaat Nashed
(74) Attorney, Agent, or Firm — Sterne, Kessler, Goldstein & Fox P.L.L.C.

(57) ABSTRACT

The present invention relates to a novel YlMPO1 gene which plays an important role in mannosylphosphorylation of an industrial yeast *Yarrowia lipolytica*, and to a method for preparing a host system capable of producing recombinant glycoproteins free of mannosylphosphate by disruption of the gene. The mannosylphosphorylation is suppressed by the disruption of YlMPO1 gene according to the present invention, thereby achieving humanization of glycosylation pathway of *Yarrowia lipolytica*.

7 Claims, 8 Drawing Sheets

[Fig. 1]

```
    -100                                                                                                                   -1
    cagccgcagacactgtcatgtatcgtgcccacgttcttactaactcagggacattgaaaaacaaacgcatcggtcgccgtaccgctcgaaagcactgagc atg gtg ctg cac ccg ttt cgc ctg ctg cgc aca tct ctt gtg agc aag ctc gtc gtc att ctc ata acc tgt ctg att ttc ggc    84
    Met Val Leu His Pro Phe Arg Leu Leu Arg Thr Ser Leu Val Ser Lys Leu Val Val Ile Leu Ile Thr Cys Leu Ile Phe Gly    28 agc tta ctc aac ttg acc gac aag ctg ccc gac gga gtc aag tca cgg gtc gcc tac atg acc gac gtg ggc tta gtc agc ggc   168
    Ser Leu Leu Asn Leu Thr Asp Lys Leu Pro Asp Gly Val Lys Ser Arg Val Ala Tyr Met Thr Asp Val Gly Leu Val Ser Gly    56 ggt gcc cgc tcg aaa gcc atg gcc ggc aac tcg tct gtg cgc atc agt cac gtg cca ctg acg aaa atc aag ttt gcc gaa aac   252
    Gly Ala Arg Ser Lys Ala Met Ala Gly Asn Ser Ser Val Arg Ile Ser His Val Pro Leu Thr Lys Ile Lys Phe Ala Glu Asn    84 gaa aag gaa ttc aac ccc aag tgg gcc cag aag aag gct ctg gac tcg tcg tcg gat tac tca ttc gag tgg aaa gac tgg gtc   336
    Glu Lys Glu Phe Asn Pro Lys Trp Ala Gln Lys Lys Ala Leu Asp Ser Ser Ser Asp Tyr Ser Phe Glu Trp Lys Asp Trp Val   112 gac ttg acc gag gtc acg ggt cta ttc aga gcc atc gag gtc ggc tcg tgt ggc aaa aac aaa caa tgc ctt agt aag ctc cag   420
    Asp Leu Thr Glu Val Thr Gly Leu Phe Arg Ala Ile Glu Val Gly Ser Cys Gly Lys Asn Lys Gln Cys Leu Ser Lys Leu Gln   140 gtc acc cga ccc ccg act cag gtg gag ccc cag gcg ttt ttc aac cgg gtc gga aag gtg ttt ttg gac cag acc atg ccc aag   504
    Val Thr Gly Pro Pro Thr Gln Val Glu Pro Gln Ala Phe Phe Asn Arg Val Gly Lys Val Phe Leu Asp Gln Thr Met Pro Lys   168 ccg aaa cag ttg att tat ctg acc gag aaa gag tca cgt ggc aag cgg gag gag ccc gtc gag ata gag tca cat gtt ccg gtg   588
    Pro Lys Gln Leu Ile Tyr Leu Thr Glu Lys Glu Ser Arg Gly Lys Arg Glu Glu Pro Val Glu Ile Glu Ser His Val Pro Val   196 gtt cgg gag cct gag ttg ggc gac ttt agc cga tcg cgt gac gcc aag tca atc caa aat gct aag cgg gag gcg act gag gag   672
    Val Arg Glu Pro Glu Leu Gly Asp Phe Ser Arg Ser Arg Asp Ala Lys Ser Ile Gln Asn Ala Lys Arg Glu Ala Thr Glu Glu   224 gcg act ggt gag tca gcc aac gag ggc cag tca cgt gac tcc gca cga gcc tcc gcg cgt gac att gcc ttt tcc gag gct gac   756
    Ala Thr Gly Glu Ser Ala Asn Glu Gly Gln Ser Arg Asp Ser Ala Arg Ala Ser Ala Arg Asp Ile Ala Phe Ser Glu Ala Asp   252 ccc gtg cac gaa gac tcg tat gac gac gac gaa aac gga acc att ctc gtg ccg acg gct gag tca gag gag gag ctc cag gaa   840
    Pro Val His Glu Asp Ser Tyr Asp Asp Asp Glu Asn Gly Thr Ile Leu Val Pro Thr Val Asp Ser Glu Glu Leu Gln Glu   280 tac gca gac aag gac gcg gcc gcc aag tcg tac ctg cga gag ggc tgg tca cgt ggc cag aaa tat gtc gag ctg ccc cgc gag   924
    Tyr Ala Asp Lys Asp Ala Ala Ala Lys Ser Tyr Leu Arg Ser Gly Trp Ser Arg Gly Gln Lys Tyr Val Glu Leu Pro Arg Glu   308 ctg ttc act tgg gac att cac gaa gag att gac aag gga ctg act aag aag agc gtt gac tca gac gac ccg tca cgt gag cag  1008
    Leu Phe Thr Trp Asp Ile His Glu Glu Ile Asp Lys Gly Leu Thr Lys Lys Ser Val Asp Ser Asp Asp Pro Ser Arg Glu Gln   336 gtt gcg cac tcg cag ttt ctt agt cag cat tgg aaa cac atc aaa aag tcc ggc aag cat ttc tcc gaa gcg tgg gtt gtg ggc  1092
    Val Ala His Ser Gln Phe Leu Ser Gln His Trp Lys His Ile Lys Lys Ser Gly Lys His Phe Ser Glu Ala Trp Val Val Gly   364 gac acc aaa gca gcc gga gtc cat tac gac tgg cga ttt ttc agc gag tta aac acc att gac gag aaa cga gtc atc ttg cgt  1176
    Asp Thr Lys Ala Ala Gly Val His Tyr Asp Trp Arg Phe Phe Ser Glu Leu Asn Thr Ile Asp Glu Lys Arg Val Ile Leu Arg   392 aaa ttg gtg cgt gcg tgg ctc gac ttc acg tca cgt gag ggc att atc acg tgg ctg gcg cat ggc acg ttg ctg ggc tgg tac  1260
    Lys Leu Val Arg Ala Trp Leu Asp Phe Thr Ser Arg Glu Gly Ile Ile Thr Trp Leu Ala His Gly Thr Leu Leu Gly Trp Tyr   420 tgg aac ggc cag tct ctg ccg tgg gat ttc gac ggt gat gtc cag atg ccg atc cgc gaa ttc gac cgg ttt gcc cgc ctc tat  1344
    Trp Asn Gly Gln Ser Leu Pro Trp Asp Phe Asp Gly Asp Val Gln Met Pro Ile Arg Glu Phe Asp Arg Phe Ala Arg Leu Tyr   448 aat cag tcg ttg gta att gat gag tca gcc ggc ggc cgg tat tat gtc gat gtg ggt ccc tcc tac gtc gag cgc ctc cga ggc  1428
    Asn Gln Ser Leu Val Ile Asp Glu Ser Ala Gly Gly Arg Tyr Tyr Val Asp Val Gly Pro Ser Tyr Val Glu Arg Leu Arg Gly   476 aac ggc aag aat gtc att gat gct cgg ttt atc gac gtt gat agt ggc atg tac att gac att acc gcc ttg gcg tat gcc gag  1512
    Asn Gly Lys Asn Val Ile Asp Ala Arg Phe Ile Asp Val Asp Ser Gly Met Tyr Ile Asp Ile Thr Ala Leu Ala Tyr Ala Glu   504 cag cag gaa aag ttc cac tgc aaa aac tgg cat cgg tat gag ttg gag agc gtt tct ccg ctg cgt cgg acg ctg ttt gag ggc  1596
    Gln Gln Glu Lys Phe His Cys Lys Asn Trp His Arg Tyr Glu Leu Glu Ser Val Ser Pro Leu Arg Arg Thr Leu Phe Glu Gly   532 aag gag gct tac att cca aac aat ttc gag tcc act ttg aac cag gag tac aag aag gcg ccg ctg gtg aac acc cgg ttc gag  1680
    Lys Glu Ala Tyr Ile Pro Asn Asn Phe Glu Ser Ile Leu Asn Gln Glu Tyr Lys Lys Ala Pro Leu Val Asn Thr Arg Phe Glu   560 ggc cac ttc tgg aac aag ttt atc aaa atg tgg gtt cag cag gac cag tgt gaa atg tta cag att gag gag aat gtg gac cag  1764
    Gly His Phe Trp Asn Lys Phe Ile Lys Met Trp Val Gln Gln Asp Gln Cys Glu Met Leu Gln Ile Glu Glu Asn Val Asp Gln   588 cgg gca gtg agg gaa aac ggt gaa ccc aca act ttt ggc gct tgt tat cga ccg gag tat ctc aag agg tat cac gag acc cac  1848
    Arg Ala Val Arg Glu Asn Gly Glu Pro Thr Thr Phe Gly Ala Cys Tyr Arg Pro Glu Tyr Leu Lys Arg Tyr His Glu Thr His   616 aag atg agt aag gct cat gag ggg gag atg gag gca atc agg caa aag gcc gat gtt tgg gaa tgg att cgc cag gag ttt gag  1932
    Lys Met Ser Lys Ala His Glu Gly Glu Met Glu Ala Ile Arg Gln Lys Ala Asp Val Trp Glu Trp Ile Arg Gln Glu Phe Glu   644 tag 1935
    ... 644 aaggggtgacggcgtgagagaggtcacgtgagaacatcacatgaggaaagggatccaggagagaccagagcacgtggattgtagctcacctcagagatgg
```

[Fig. 2]

```
NcMnn4p     1  ---------------MWSSLTPAR QATTTSWRDR  LT LMA TFVLS  ASP  PIEGAVV
AfMnn4p     1  ------------------------------IPR  LR IVLAIWSAEA  ASP RSS----
YlMpo1p     1  -----MVLHPFRLLRTS VSKLVVIL TC FGS  LN TDK LPDGVK SRVAY TDVGLVS
PpPho1p     1  --------------MTLRSA KARTS GL GA  IAS  FFTTVTFYDESK VGI RVSDTYT
ScMnn4p     1  --------------MLQR SSKLH RF SG  RVKHYP RRI LPLILLQIII TFIWSNS
CaMnn4p     1  ---MSNTIPQYFIRIFN IFSAR KNFQLA ISG LFFGSFAILSTT SYSKKFNYFDDLI
PpMnn4Ap    1  -----------MKVSKR IPRRS LL MM  LVVYQL VLV LGLESV SEGKLASLLDLGD
PpMnn4Bp    1  --------MFKETSKNLFGSINTFNT EY  YMM LLTAYF LNHLLH S DNINHLVESDV
PpMnn4Cp    1  MSGNPFLFSPSNFDFSG DHYRSTDKDHLA DVLDYDKNHFFSRNSP S KSR HFYRHKL

NcMnn4p    47  KANNNDA S-------------------------------------QPQAQAQAKAE
AfMnn4p    27  ------------------------------------------------DQDHSN
YlMpo1p    56  GGARSKA A------------------------------------GNSSVRISHVP
PpPho1p    50  GHSAVSSTFN---------------ASSVVSDNKINGYGLPLIDTESNSRYEDPDDISIEN
ScMnn4p    48  PQRNGLGRDA--------------DYLLPNYNELDSDDDSWYSILTSSFKNDRKIQFAKT
CaMnn4p    58  LKIYDYNYLTNNYNIDYLAKNDPEAYFNVKVQQIVDEKKQHDLESKFWSLDTKINDDQAT
PpMnn4Ap   50  WDLANSS SIS--------------------DFIKLKLKGQKTYHKFDEHVFAAMAR
PpMnn4Bp   53  NYQLLQR TN------------------------------------KVKLFDEEAVL
PpMnn4Cp   61  TTRKQIG FSG----------------RLKLFVLALFVLITFSAIHIPIPFSLDILGSH

NcMnn4p    67  RQFSAPAQAQEA PATATTSDDT NT-----------------------------------
AfMnn4p    33  NHGKILTHEPEY PLWEKYGLNK S----------------------------------
YlMpo1p    76  TKIKFAENEKEFNPKWAQKKA TD SSSDYSFEWKDWVDLTEVTG LFRA EVGSCGKNKQC
PpPho1p    96  ELRYRIAQSTKEF NMWKLDTT TEAS KIPNIQSFELQPFKER LDNS YNSKNIGNFYF
ScMnn4p    94  YENLKFGTNPKWVNEYTLQND I SVK GPRKGSKLESVDELKFYDFDPRLTWSVVLNHL
CaMnn4p   118  QIPAYFTYNKPR NKNLEDSEQS SKP EKPLIQPFDPRFTLAMYYYY DQQMTTAHHDS
PpMnn4Ap   87  QSNENGKLADYESTSSKTDVT QNVE WKRLSEEEYTYEPRITT AVY SYIHQRTYDRY
PpMnn4Bp   74  PFAKNLNRRTERF PRLPVAAY TRSLQDQYSELPQGTDLNDIPP TEVSFHWDDWLSLGIA
PpMnn4Cp  104  KYLPLREKVDPE ALHLHGLD LSVAE PFFNDDMMSEFNYDPR LPTA ILKLVLDHISV

NcMnn4p    94  ------------------------------------------------------------
AfMnn4p    58  ------------------------------------------------------------
YlMpo1p   136  LSKLQVTGPPTQVEPQA FNRVGKVFLDQTMPKPKQLIYLTEKESRGKREEPVEIESHVP
PpPho1p   156  YDPRLTFSVY K IKDKLASGSTT LT PFNWAHFRDLSSLNPYLDIKQEDKVACDYFYE
ScMnn4p   154  QNNDADQPEK P SWYD TTFHEL KL SIDKTVLPCNFLFQSAFDKESLEAIETELGEP
CaMnn4p   178  SSSSSGNSIT P NWYD VDMSVL KY LAPNKDKPDCSILDAHEDARKIETEKKKMEKL
PpMnn4Ap  147  ATSYAPYNLR P SWAD IDLTAL QY DKTKGCEAVFPRESEATMKLNNITVVDWLEGL
PpMnn4Bp  134  STFWDAFDNYNKRQGENAISYEQL AI VNDLEDFSPYTAHILHSNVEVYKYRTIPQKIV
PpMnn4Cp  164  RNGTFDAKFK P NWKL VDLHSRLVP SNSWYNRFRLPSGRFETCDEFKRFFGITKNHFG

NcMnn4p    94  ------------------------------------------------------------
AfMnn4p    58  ------------------------------------------------------------
YlMpo1p   196  VVREPELGDFSRSRDAKSIQNAKREATEEATGESAN-------------------------
PpPho1p   216  SSNKDKRKPTGNCIEFKDVRDEHLIQYGISSKDHLPGP-----------------------
ScMnn4p   214  LFLYERPKYAQKLWYKAARNQDRIKDSKELKKHCSKLF-----------------------
CaMnn4p   238  AKQWDENKRKAEEEKKKAEEDKKKEEEEKKKAEEEEEKQRHEQEKQALEEDKKKLEEEKKK
PpMnn4Ap  207  CITDKSLQNSVNSTYAEEINSRDILSPNFHVFGYSDAK-----------------------
PpMnn4Bp  194  YMSNKGYFELLVTE----------------------------------------------
PpMnn4Cp  224  TDLDNCVDIEYDTPEGYPKFKVLHAEDKALPYEARIIYG---------------------

NcMnn4p    94  ------------------------------------------------------------
AfMnn4p    58  ------------------------------------------------------------
YlMpo1p   232  ------------------------------------------------------------
PpPho1p   254  -----------------------------------------------------FILKSL
ScMnn4p   252  ------------------------------------------------------TPDGHG
CaMnn4p   298  IEEEKNKLQEQQQQQQQQEEKANDGNQEHSKFVKRDDEIKMSTSQDKSDSDADRAKIDMTT
PpMnn4Ap  245  -----------------------------------------------------------D
PpMnn4Bp  208  ------------------------------------------------------------
PpMnn4Cp  263  ------------------------------------------------------------

NcMnn4p    94  -----------------------------------------NTD DDPLLPERKY F E
AfMnn4p    58  ----------------------------------------------QEFKY F E
YlMpo1p   232  -----------------------------EGQSRDSARASARDIAFSEADPV E
PpPho1p   260  GIPMQHTAKRLESNLYLLTGAPVPLSLSFMTKKGLYQVGVDQTGKL PNIARTELWE EYK
ScMnn4p   258  SPKGLRFNTQFQIKELYDKVRPEVYQLQARNYILTTQSHPLSISII SDNSTYQVPLQTE
CaMnn4p   358  FFNEAFEKLSDEDKASVAKDVEDAVKKITQPSSWCVPNAKLSIDHS KQIVHPGFNVE S
PpMnn4Ap  246  NPQQKIFQSKSYINSKLPLPKSLIFLTDGGSYALTVDRTQNKRILKSGLLSHFFSKKK E
PpMnn4Bp  208  -----------------------------------------K KLSNEGLWSI Q
PpMnn4Cp  263  ---------ASYLYHEAQNPKRLIFLGLGKSNESLILPVEANDSSNLMQFNHEYARS EN

NcMnn4p   111  PGWTEELS----------------------------------------------------
AfMnn4p    66  PGNDDILG----------------------------------------------------
YlMpo1p   257  DSYDDDENGTILVPTAESEEELQEYADKDAAAKSYLRSGWSRGQKY E-------------
PpPho1p   320  NGKENLQFN--AQEELSHLIETVPSSSNSSSG CYFTTE KENNFE D------------
ScMnn4p   318  KSKNLVQSGLLQEYINDNINSTNKRKKNKQDV FNHNRLFQEFVNNDQ NSLYKLEIEET
CaMnn4p   418  PGRTTPQKAIIAGKSFLYSYAPPPSSILFLTS GSYSVN QHSAPL RNGIPESYLANNN
PpMnn4Ap  306  HNLPQDQKTFTFDPVYEFNRLKSQVKPRPISS PSIDSA KENDYK K K----------
PpMnn4Bp  223  KQGGLNEFSSLNLIEEVDALDEIYDSKGLPAW PPFPEE DASDEDFKFN----------
PpMnn4Cp  314  QPFVSLEELVKKVSLTLNLNSDKVLPINELDVIKDTPRL NHNNQG S D----------
```

[Fig. 3]

```
NcMnn4p   119 ------------------------------------------------------------
AfMnn4p    74 ------------------------------------------------------------
YlMpo1p   306 ---------------------------PRELFTWDIHEEIDKGLT KSVDS DPS
PpPno1p   367 ---------------------------SKNDFTFDDSEVESLIKGLSEQDL LHT
ScMnn4p   378 DKFTF------------------DKDLVYLSPSDFKFDASKKIEELEEQ KLYPDKFSA
CaMnn4p   478 FDVSLNVLQQLHKLKKNHKPDTAKVINDYLLHIPKESFKYDPDSIIFDYT RLDKG KLT
PpMnn4Ap  356 ------------------------------ESSFIFNYGRILSNYEERL SLN
PpMnn4Bp  273 ---------------------------------ATEELA VEQIK PKL
PpMnn4Cp  364 -----------------------KSSFQWDLERELQLLE RTSQVNDVE

NcMnn4p   119 --------------------------------HYDTREF SP PYDP-------
AfMnn4p    74 --------------------------------HYDTRFF EP PDKE-------
YlMpo1p   334 REQVAHSQFLSQHWKHIKKSGKH SEAW VGDTKAAC HYD RFF ELNTIDE-------
PpPno1p   395 QRYKESLQYSFATRENDVKKYFYEARMI NTVNKEG AHYD RFFNGA NHESSGFTEEE
ScMnn4p   419 HNENYLNSLKNSVKTSPALQRKF YEAGAVKQYKGM GF RDK RFF NVDTLIND-------
CaMnn4p   538 IKELKYLQSLEYSKDKVAHGGPPKYFAESRLIGTTV GD HYD RFFN GVQFGTVD------
PpMnn4Ap  379 DFEKSHYESLAYSSLLEARKLPK FGEV LKNPQDG G IHYD RFF GL DKTQIN-HFED
PpMnn4Bp  289 EDIFYQEGLQHGIQTLPSDASVY PVNY ENDPGLQ SH HLI PFF GM LPREIH-----
PpMnn4Cp  390 GLDAGIYSTIQCEMRSMYDFSKY HESK SGKYLPS GE HYD RFFN GFYLSQQEN-----

NcMnn4p   134 ----LVHL L RS LMTSSRS TW AHGTLLGWYWNGA IMPWDYD DVQ SNITG
AfMnn4p    89 ----SET T RA INFFNERG FTW AHGTLLGW WNGKVI PWDWDI TQ LDTTLL
YlMpo1p   387 ----RVI L RAWLDE TSREG TW AHGTLLGWYWNGQSL PWDFDG DVQMPI REFD
PpPno1p   455 RQLR RSV L RNWLVFNYQQGS PTW AHGTLLS WYWNS MF PWDYDI DVQMPI KSIN
ScMnn4p   472 -KQEYQAR NS RT QKFTKANG TW SHGTLYG LTNG AFPWDNDF D QMPI KHLQ
CaMnn4p   592 ----QSLT L RTWLSFTRKSC TW AHG LLSWYWNG AFPWDNDI DVQI PIMDLH
PpMnn4Ap  438 ETER KII L RTWQYFTYHNN INW SHG LLSWYWNG SF PWDNDI DVQMPI MFLN
PpMnn4Bp  344 ------SS YN A FLFARQHGYVWFFYGNL GWY NGNNH PWDSDIDA IMP AEA
PpMnn4Cp  445 -----LAVL LGRAW LRF RAAG HTW AHGTLLGWYWNG ILPWDQD DVQMT QSLY

NcMnn4p   190 Q D NQ TFDYVYTLSEEEEKEGLGKQGEVTVK YLLDVNP WAQRT RLEG MNV IDAR
AfMnn4p   145 RL D FNQ VHYTAA SSVER-------------SYLL DVNP ARQRERG CLNI IDAR
YlMpo1p   443 RF L NQSLV SAGG-----------------Y DVGPSYVER LRGNG KNV IDAR
PpPno1p   515 NLCA FNQSI E LT C----------------YSS LDCGSSITHRT CKCLNF IDAR
ScMnn4p   531 LLSQY FNQSL E PRQGN---------------G Y LDV SDSLTVR INGNG KNN IDAR
CaMnn4p   648 KLSL FNQ V E PEL GFG---------------Y LD GS ITLRE GNGNNN IDAR
PpMnn4Ap  498 NFC FN SLV E VSQGFG---------------Y LDCTS LAQRT RGNG NNN IDAR
PpMnn4Bp  398 R HHN L ENPH GYG---------------TYLL TSP FTK TR- GGHID R
PpMnn4Cp  500 LL FNSSLVT VSI DGYSSALG---------Y DVGSSFFVRD LNGNNA IDAR

NcMnn4p   250 ID NG Y DITGL SEDREETGT------------------------------
AfMnn4p   192 IDRR TGLYIDITGL SRLEPEK-------------------------------
YlMpo1p   486 FIDV G YIDIT LAYAEQQE--------------------------------
PpPno1p   560 FINV TGLYIDITGL ST QSARPPRF----------------------------
ScMnn4p   576 FIDV TGLYIDITGLAS SAPSRDYLNSYIEERLQEEHLDINNIPESNGETATLPDKVDD
CaMnn4p   693 FID TGLYIDITG LAL NSETPKSDLAELPKN-----------------------
PpMnn4Ap  543 FIDVS GL IDITGLAL GSTMPKRYSNKLIKQPKKSTDSTG------------------
PpMnn4Bp  441 F DVKRG TYID SAMHGIYPDWVRDG------------------------------
PpMnn4Cp  550 F DT TGLY DIT LAF DHLKLKLTTKEKVELQKVMDPNVKEKLQWIKNKYSTATLPG-

NcMnn4p   274 ------------------------------------------------------------
AfMnn4p   214 ------------------------------------------------------------
YlMpo1p   508 ------------------------------------------------------------
PpPno1p   586 ------------------------------------------------------------
ScMnn4p   636 GLVNMATLNITELRDYITSDENKNHKRVPTDTDLKDLLKKELEELPKSKTIENKLNPKQR
CaMnn4p   726 ---------------------------------------------------FEIKDNNY
PpMnn4Ap  585 --------------------------------------------------STPENGLTRN
PpMnn4Bp  470 ------------------------------------------------------------
PpMnn4Cp  609 ----------------------------------------VIETDRNKVSDALEKQFHDFK

NcMnn4p   274 ------RQG SD NYHGYGTRC WPLR TEFEGVEA PW VEEL KEEY GVKS-L EES
AfMnn4p   214 ------PS D NDHKYQTG YPLR TTFEGVPAKLPL LIKEYTQEA-L STK
YlMpo1p   508 --------K HC NWHRYELES SPLR T FECKEA IENN E I NQEYKKAP-L VNTR
PpPno1p   586 SNASKKDP CRNNHFYSHNN APL YT MEGVPS IPQO EEL IREEYTTG--L SKH
ScMnn4p   696 YFLNEKLK CRNNHFNSFE SPLINT EHGVPALI PHRHTYC LHNEYHVPDRYAFDA
CaMnn4p   734 KPANELLQ CRNNHFNSYD SPLM SVEGEI IFSR S I TREYRSG--L SNS
PpMnn4Ap  595 LRQNLNAQ CRNGHFYQYS SPL L VEGALTLIPN V I LETEYQRRG-LEKNT
PpMnn4Bp  470 VKENPKNLALAD NGN YLTR LPLR T FEGSRS TVK LEDT LRNYGDKV-L INTE
PpMnn4Cp  630 FDNFVNKE HCRNNHFYKYG GRLRS T FEGVPAL IF E I LKREYPKG--L LKH

NcMnn4p   328 AGHQ DHGR QWVKT--------------------------------
AfMnn4p   267 HNHT YPD EQWV SDH-------------------------------
YlMpo1p   559 EGHF NKF N W QQ-----------------------------------
PpPno1p   644 NGNF MTQN NW ER-----------------------------------
ScMnn4p   756 KNTA LPEF FWFDY GLKKCSNINSWYPNIPSINSWNPNLLKEISSTKFESKLFDSNK
CaMnn4p   792 HGGYI IAK WVKE DLYYFIKHRDQWTKYHSFN-----------------
PpMnn4Ap  654 AKYL VPE W SYNDIYDILQGTNSHGRPLSAKTMATIFPRLN--------------
PpMnn4Bp  529 LAD E HDDW WVQKK----------------------------------
PpMnn4Cp  688 SNHF DPVN WVPEK-----------------------------------
```

[Fig. 4]

```
NcMnn4p    345  ------------------------------------------------------------
AfMnn4p    284  ------------------------------------------------------------
YlMpo1p    576  ------------------------------------------------------------
PpPno1p    661  ------------------------------------------------------------
ScMnn4p    816  VSEYSFKNLSMDDVRLIYKNIPKAGFIEVFTNLYNSFNVTAYRQKELEIQYCQNLTFIEK
CaMnn4p    828  ------------------------------------------------------------
PpMnn4Ap   700  ------------------------------------------------------------
PpMnn4Bp   546  ------------------------------------------------------------
PpMnn4Cp   705  ------------------------------------------------------------

NcMnn4p    345  ------------------------------------------------------------
AfMnn4p    284  ------------------------------------------------------------
YlMpo1p    576  ------------------------------------------------------------
PpPno1p    661  ------------------------------------------------------------
ScMnn4p    876  KKLLHQLRINVAPKLSSPAKDPFLFGYEKAMWKDLSKSMNQTTLDQVTKIVHEEYVGKII
CaMnn4p    828  ------------------------------------------------------------
PpMnn4Ap   700  ------------------------------------------------------------
PpMnn4Bp   546  ------------------------------------------------------------
PpMnn4Cp   705  ------------------------------------------------------------

NcMnn4p    345  ------------------------------------------------------------
AfMnn4p    284  ------------------------------------------------------------
YlMpo1p    576  ------------------------------------------------------------
PpPno1p    661  ------------------------------------------------------------
ScMnn4p    936  DLSESLKYRNFSLFNITFDETGTTLDDNTEDYTPANTVEVNPVDFKSNLNFSSNSFLDLN
CaMnn4p    828  ------------------------------------------------------------
PpMnn4Ap   700  ------------------------------------------------------------
PpMnn4Bp   546  ------------------------------------------------------------
PpMnn4Cp   705  ------------------------------------------------------------

NcMnn4p    345  ------------------------LA----------------------------------
AfMnn4p    284  ------------------------DEIAKG-------------------------K
YlMpo1p    576  ------------------------QCEMLQ-------------------------IE
PpPno1p    661  ---------------------PMLALVPSSKYEIEGGGVDHNKIIKSILE
ScMnn4p    996  SYGLDLFAPTLSDVNRKGIQMFDKDPIIVYEDYAYAKLLEERKRREKKKKEEEEKKKKEE
CaMnn4p    828  ------------TKLSQDPSNTLLQDYSYLMSEQEYENLQYSTDLEHDNPFKKTKKPLE
PpMnn4Ap   700  ----------------SDINLKKFLRNDHTFKNIYSTFNVTRVHEEELKHLIVNYDQ
PpMnn4Bp   546  -----------------------------------------KYCTYEEFEDY
PpMnn4Cp   705  ---------------------------------------------------KKK

NcMnn4p         ------------------------------------------------------------
AfMnn4p    292  NDDRQYER-----------------------------------------------------
YlMpo1p    584  ENVDQRAV NGEPTTFGACYRP YLKRYHETHKMSKAHEG MEAIRQKADVWEWIREEF
PpPno1p    691  SNIKKI LL DNPDILEEVIRTY LTSIHHKEMQYLSSVKP GDRSMQSNDITSSYQEFL
ScMnn4p   1056  EEKKKK EE KKKKEEEKKKKE EEKKKKEEEEKKKQEEE KKKKEEEEKKKQEEGEKM
CaMnn4p    876  KNSELEKI HMNESELLQFLNND ILIQFFNAKEFTSFHES EIMQLTFGKSTAKLMSSAI
PpMnn4Ap   741  NKRKSA EY QFLENLRFMNPIRK LVTYESRLKALDGYNEV ELEKKQENREKERKEKKE
PpMnn4Bp   558  SAHGGV EYD DGVLTLEGACGFE VRQDWIITRESVNLHMK EWAIQRNESTTEYTAKDL
PpMnn4Cp   709  RHIEFSLT VTESHKKELAQIHGNETGITSDFAYSPFRIDPWLSRYRKKMTRSQ-----

NcMnn4p         ------------------------------------------------------------
AfMnn4p         ------------------------------------------------------------
YlMpo1p    644  E-----------------------------------------------------------
PpPno1p    751  ASLKKFQPLRKDLFQFERIDLSKHRKQ---------------------------------
ScMnn4p   1116  KNEDEENKKNEDEEKKKNEEEEKKKQEEKNKKNEDEEKKKQEEEEKKKNEEEEKKKQEEG
CaMnn4p    936  DFPPIKYEPYLYKLNHDLDTFENKVDRYLALQDAYQQEHNNSPSGGSDNGFMEIEEDLDF
PpMnn4Ap   801  KEEKEKKEKEEKEKKEKEEKEKKEKEEKERKEKEEKEEYEEDDNEGEQPTEQKSQQEAKE
PpMnn4Bp   618  PRYRPDSFKNLLDGVSNHGNGNVGKIEHVKLEHND-------------------------
PpMnn4Cp        ------------------------------------------------------------

NcMnn4p         ---
AfMnn4p         ---
YlMpo1p         ---
PpPno1p         ---
ScMnn4p   1176  HSN
CaMnn4p    996  AF-
PpMnn4Ap   861  ---
PpMnn4Bp        ---
PpMnn4Cp        ---
```

[Fig. 5]
A.
| | YlMpo1p (644 aa) | ScMnn4p (1178 aa) | CaMnn4p (997 aa) | PpPno1p (777 aa) | PpMnn4Ap (860 aa) | PpMnn4Bp (652 aa) | PpMnn4Cp (763 aa) | NcMnn4p (346 aa) | AfMnn4p (300 aa) |
|---|---|---|---|---|---|---|---|---|---|
| YlMpo1p | | 40 | 34 | 33 | 32 | 27 | 33 | 41 | 37 |
| ScMnn4p | 58 | | 29 | 25 | 26 | 29 | 25 | 33 | 31 |
| CaMnn4p | 57 | 46 | | 35 | 36 | 28 | 32 | 32 | 35 |
| PpPno1p | 54 | 40 | 50 | | 31 | 23 | 29 | 32 | 33 |
| PpMnn4Ap | 49 | 42 | 53 | 49 | | 21 | 27 | 27 | 28 |
| PpMnn4Bp | 45 | 51 | 50 | 42 | 40 | | 23 | 29 | 32 |
| PpMnn4Cp | 47 | 44 | 47 | 44 | 44 | 40 | | 32 | 32 |
| NcMnn4p | 56 | 53 | 46 | 50 | 47 | 46 | 45 | | 47 |
| AfMnn4p | 55 | 45 | 49 | 50 | 42 | 50 | 45 | 61 | |
← Similarity    Identity →
B.
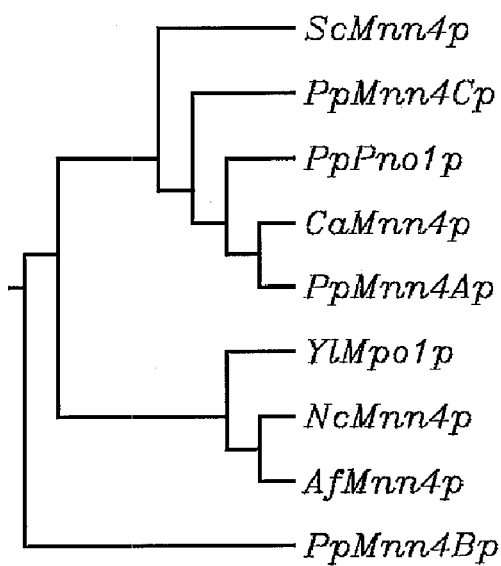

[Fig. 6]
A.
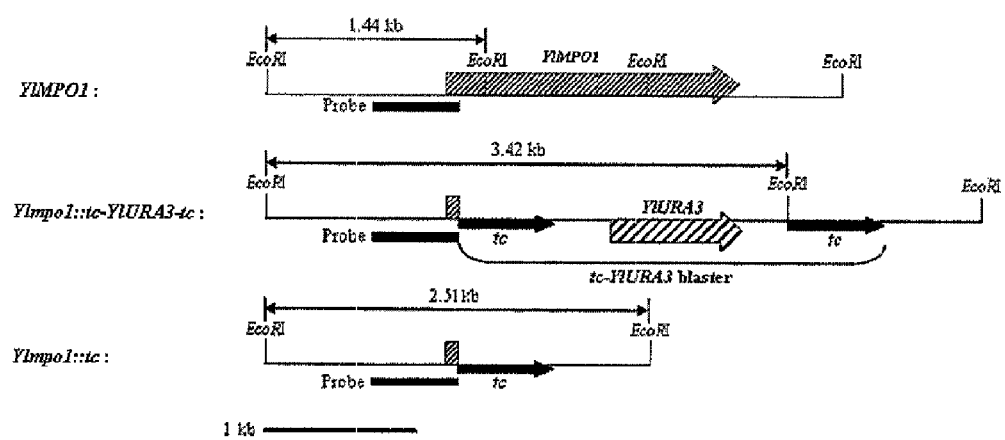
B.
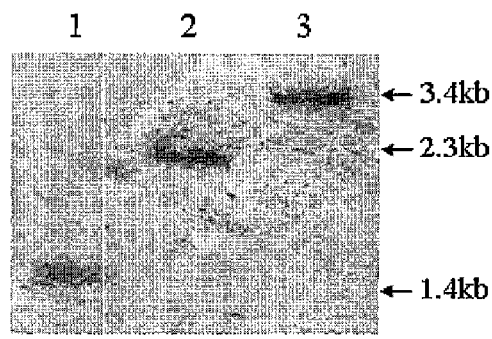

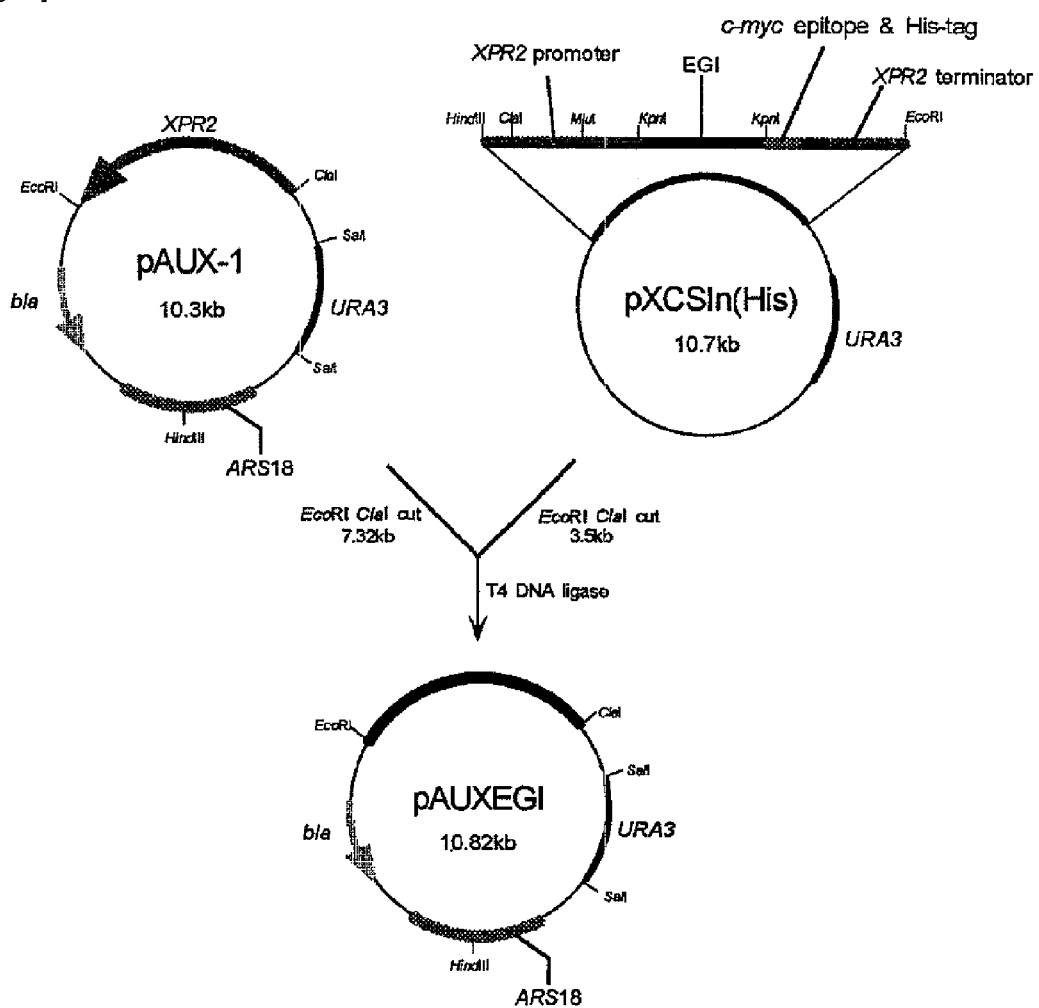
[Fig. 7]

[Fig. 8]
A.
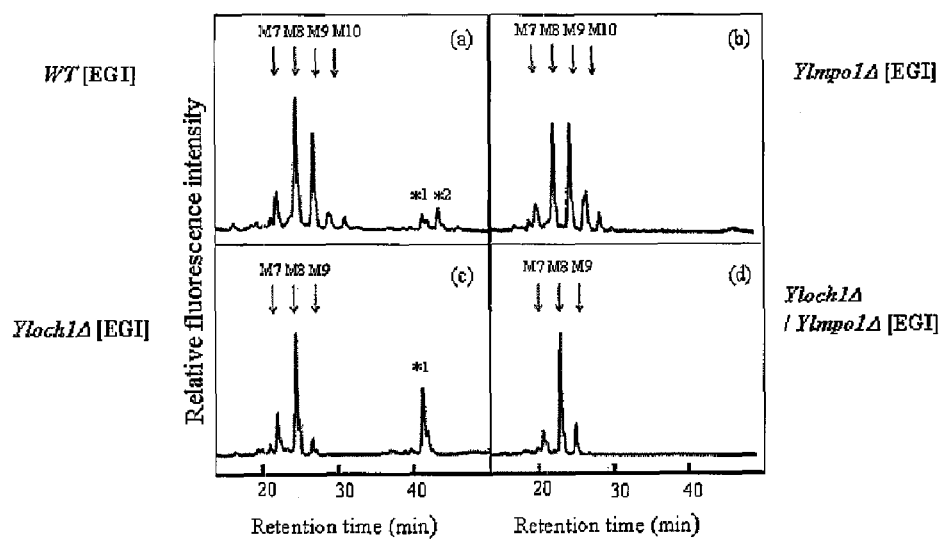
B.
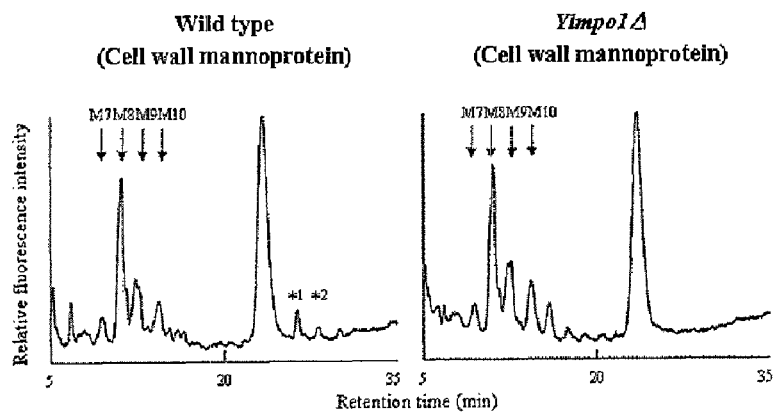
C.
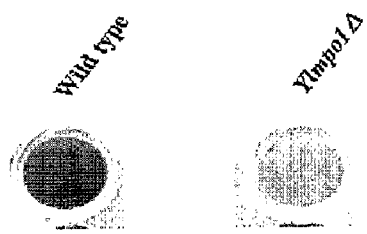

SEQUENCE LISTING

```
<160> NUMBER OF SEQ ID NOS: 20

<210> SEQ ID NO 1
<211> LENGTH: 2135
<212> TYPE: DNA
<213> ORGANISM: Yarrowia lipolytica

<400> SEQUENCE: 1
cagccgcaga cactgtcatg tatcgtgccc acgttcttac taactcaggg acattgaaaa      60
acaaacgcat cggtcgccgt accgctcgaa agcactgagc atggtgctgc acccgtttcg     120
cctgctgcgc acatctcttg tgagcaagct cgtcgtcatt ctcataacct gtctgatttt     180
cggcagctta ctcaacttga ccgacaagct gcccgacgga gtcaagtcac gggtcgccta     240
catgaccgac gtgggcttag tcagcggcgg tgcccgctcg aaagccatgg ccggcaactc     300
gtctgtgcgc atcagtcacg tgccactgac gaaaatcaag tttgccgaaa acgaaaagga     360
```

```
attcaacccc aagtgggccc agaagaaggc tctggactcg tcgtcggatt actcattcga    420
gtggaaagac tgggtcgact tgaccgaggt cacgggtcta ttcagagcca tcgaggtcgg    480
ctcgtgtggc aaaaacaaac aatgccttag taagctccag gtcaccggac ccccgactca    540
ggtggagccc caggcgtttt tcaaccgggt cggaaaggtg ttttttggacc agaccatgcc    600 caagccgaaa cagttgattt atctgaccga gaaagagtca cgtggcaagc gggaggagcc    660
cgtcgagata gagtcacatg ttccggtggt tcgggagcct gagttgggcg actttagccg    720
atcgcgtgac gccaagtcaa tccaaaatgc taagcgggag gcgactgagg aggcgactgg    780
tgagtcagcc aacgagggcc agtcacgtga ctccgcacga gcctccgcgc gtgacattgc    840
cttttccgag gctgaccccg tgcacgaaga ctcgtatgac gacgacgaaa acggaaccat    900
tctcgtgccg acggctgagt cagaggagga gctccaggaa tacgcagaca aggacgcggc    960
cgccaagtcg tacctgcgaa gcggctggtc acgtggccag aaatatgtcg agctgccgcg   1020
cgagctgttc acttgggaca ttcacgaaga gattgacaag ggactgacta agaagagcgt   1080
tgactcagac gacccgtcac gtgagcaggt tgcgcactcg cagtttctta gtcagcattg   1140
gaaacacatc aaaaagtccg gcaagcattt ctccgaagcg tgggttgtgg cgacaccaa    1200 agcagccgga gtccattacg actggcgatt tttcagcgag ttaaacacca ttgacgagaa   1260
acgagtcatc ttgcgtaaat tggtgcgtgc gtggctcgac ttcacgtcac gtgagggcat   1320
tatcacgtgg ctggcgcatg gcacgttgct gggctggtac tggaacggcc agtctctgcc   1380
gtgggatttc gacggtgatg tccagatgcc gatccgcgaa ttcgaccggt ttgcccgcct   1440
ctataatcag tcgttggtaa ttgatgagtc agccggcggc cggtattatg tcgatgtggg   1500
tccctcctac gtcgagcgcc tccgaggcaa cggcaagaat gtcattgatg ctcggtttat   1560
cgacgttgat agtggcatgt acattgacat taccgccttg gcgtatgccg agcagcagga   1620
aaagttccac tgcaaaaact ggcatcggta tgagttggag agcgtttctc cgctgcgtcg   1680
gacgctgttt gagggcaagg aggcttacat tccaaacaat ttcgagtcca ttttgaacca   1740
ggagtacaag aaggcgccgc tggtgaacac ccggttcgag ggccacttct ggaacaagtt   1800
tatcaaaatg tgggttcagc aggaccagtg tgaaatgtta cagattgagg agaatgtgga   1860
ccagcgggca gtgagggaaa acggtgaacc cacaactttt ggcgcttgtt atcgaccgga   1920
gtatctcaag aggtatcacg agacccacaa gatgagtaag gctcatgagg gggagatgga   1980
ggcaatcagg caaaaggccg atgtttggga atggattcgc gaggagtttg agtagaaggg   2040
gtgacggcgt gagagaggtc acgtgagaac atcacatgag gaaagggatc caggagagac   2100
cagagcacgt ggattgtagc tcacctcaga gatgg                              2135
```

<210> SEQ ID NO 2
<211> LENGTH: 644
<212> TYPE: PRT
<213> ORGANISM: Yarrowia lipolytica

<400> SEQUENCE: 2

```
Met Val Leu His Pro Phe Arg Leu Leu Arg Thr Ser Leu Val Ser Lys
1               5                   10                  15

Leu Val Val Ile Leu Ile Thr Cys Leu Ile Phe Gly Ser Leu Leu Asn
            20                  25                  30

Leu Thr Asp Lys Leu Pro Asp Gly Val Lys Ser Arg Val Ala Tyr Met
        35                  40                  45

Thr Asp Val Gly Leu Val Ser Gly Gly Ala Arg Ser Lys Ala Met Ala
    50                  55                  60
```

-continued

Gly Asn Ser Ser Val Arg Ile Ser His Val Pro Leu Thr Lys Ile Lys
65                  70                  75                  80

Phe Ala Glu Asn Glu Lys Glu Phe Asn Pro Lys Trp Ala Gln Lys Lys
                85                  90                  95

Ala Leu Asp Ser Ser Asp Tyr Ser Phe Glu Trp Lys Asp Trp Val
            100                 105                 110

Asp Leu Thr Glu Val Thr Gly Leu Phe Arg Ala Ile Glu Val Gly Ser
            115                 120                 125

Cys Gly Lys Asn Lys Gln Cys Leu Ser Lys Leu Gln Val Thr Gly Pro
    130                 135                 140

Pro Thr Gln Val Glu Pro Gln Ala Phe Phe Asn Arg Val Gly Lys Val
145                 150                 155                 160

Phe Leu Asp Gln Thr Met Pro Lys Pro Lys Gln Leu Ile Tyr Leu Thr
                165                 170                 175

Glu Lys Glu Ser Arg Gly Lys Arg Glu Glu Pro Val Glu Ile Glu Ser
            180                 185                 190

His Val Pro Val Val Arg Glu Pro Glu Leu Gly Asp Phe Ser Arg Ser
        195                 200                 205

Arg Asp Ala Lys Ser Ile Gln Asn Ala Lys Arg Glu Ala Thr Glu Glu
    210                 215                 220

Ala Thr Gly Glu Ser Ala Asn Glu Gly Gln Ser Arg Asp Ser Ala Arg
225                 230                 235                 240

Ala Ser Ala Arg Asp Ile Ala Phe Ser Glu Ala Asp Pro Val His Glu
                245                 250                 255

Asp Ser Tyr Asp Asp Glu Asn Gly Thr Ile Leu Val Pro Thr Ala
            260                 265                 270

Glu Ser Glu Glu Glu Leu Gln Glu Tyr Ala Asp Lys Asp Ala Ala Ala
        275                 280                 285

Lys Ser Tyr Leu Arg Ser Gly Trp Ser Arg Gly Gln Lys Tyr Val Glu
    290                 295                 300

Leu Pro Arg Glu Leu Phe Thr Trp Asp Ile His Glu Glu Ile Asp Lys
305                 310                 315                 320

Gly Leu Thr Lys Lys Ser Val Asp Ser Asp Pro Ser Arg Glu Gln
                325                 330                 335

Val Ala His Ser Gln Phe Leu Ser Gln His Trp Lys His Ile Lys Lys
            340                 345                 350

Ser Gly Lys His Phe Ser Glu Ala Trp Val Val Gly Asp Thr Lys Ala
        355                 360                 365

Ala Gly Val His Tyr Asp Trp Arg Phe Phe Ser Glu Leu Asn Thr Ile
    370                 375                 380

Asp Glu Lys Arg Val Ile Leu Arg Lys Leu Val Arg Ala Trp Leu Asp
385                 390                 395                 400

Phe Thr Ser Arg Glu Gly Ile Ile Thr Trp Leu Ala His Gly Thr Leu
                405                 410                 415

Leu Gly Trp Tyr Trp Asn Gly Gln Ser Leu Pro Trp Asp Phe Asp Gly
            420                 425                 430

Asp Val Gln Met Pro Ile Arg Glu Phe Asp Arg Phe Ala Arg Leu Tyr
        435                 440                 445

Asn Gln Ser Leu Val Ile Asp Glu Ser Ala Gly Gly Arg Tyr Tyr Val
    450                 455                 460

Asp Val Gly Pro Ser Tyr Val Glu Arg Leu Arg Gly Asn Gly Lys Asn
465                 470                 475                 480

Val Ile Asp Ala Arg Phe Ile Asp Val Asp Ser Gly Met Tyr Ile Asp

```
                        485                 490                 495
Ile Thr Ala Leu Ala Tyr Ala Glu Gln Gln Glu Lys Phe His Cys Lys
            500                 505                 510

Asn Trp His Arg Tyr Glu Leu Glu Ser Val Ser Pro Leu Arg Arg Thr
            515                 520                 525

Leu Phe Glu Gly Lys Glu Ala Tyr Ile Pro Asn Asn Phe Glu Ser Ile
        530                 535                 540

Leu Asn Gln Glu Tyr Lys Lys Ala Pro Leu Val Asn Thr Arg Phe Glu
545                 550                 555                 560

Gly His Phe Trp Asn Lys Phe Ile Lys Met Trp Val Gln Gln Asp Gln
                565                 570                 575

Cys Glu Met Leu Gln Ile Glu Glu Asn Val Asp Gln Arg Ala Val Arg
            580                 585                 590

Glu Asn Gly Glu Pro Thr Thr Phe Gly Ala Cys Tyr Arg Pro Glu Tyr
        595                 600                 605

Leu Lys Arg Tyr His Glu Thr His Lys Met Ser Lys Ala His Glu Gly
        610                 615                 620

Glu Met Glu Ala Ile Arg Gln Lys Ala Asp Val Trp Glu Trp Ile Arg
625                 630                 635                 640

Glu Glu Phe Glu

<210> SEQ ID NO 3
<211> LENGTH: 18
<212> TYPE: DNA
<213> ORGANISM: Artificial Sequence
<220> FEATURE:
<223> OTHER INFORMATION: forward primer for pT-YIMPO1+

<400> SEQUENCE: 3
caacacacca tcggagac                                                18

<210> SEQ ID NO 4
<211> LENGTH: 36
<212> TYPE: DNA
<213> ORGANISM: Artificial Sequence
<220> FEATURE:
<223> OTHER INFORMATION: reverse primer for pT-YIMPO1+

<400> SEQUENCE: 4
ccatggatcc gtagatctct gccgaaaatc agacag                            36

<210> SEQ ID NO 5
<211> LENGTH: 36
<212> TYPE: DNA
<213> ORGANISM: Artificial Sequence
<220> FEATURE:
<223> OTHER INFORMATION: forward primer for pT-YIMPO1+

<400> SEQUENCE: 5
agatctacgg atccatggat ccaggagaga ccagag                            36

<210> SEQ ID NO 6
<211> LENGTH: 18
<212> TYPE: DNA
<213> ORGANISM: Artificial Sequence
<220> FEATURE:
<223> OTHER INFORMATION: reverse primer for pT-YIMPO1+

<400> SEQUENCE: 6
gttgcgtcat tctctcca                                                18
```

```
<210> SEQ ID NO 7
<211> LENGTH: 18
<212> TYPE: DNA
<213> ORGANISM: Artificial Sequence
<220> FEATURE:
<223> OTHER INFORMATION: linker sequence

<400> SEQUENCE: 7
agatctacgg atccatgg                                                  18

<210> SEQ ID NO 8
<211> LENGTH: 19
<212> TYPE: DNA
<213> ORGANISM: Artificial Sequence
<220> FEATURE:
<223> OTHER INFORMATION: forward primer for pT-YlOCH1+

<400> SEQUENCE: 8 acttttttgca tctgcggac                                                 19

<210> SEQ ID NO 9
<211> LENGTH: 36
<212> TYPE: DNA
<213> ORGANISM: Artificial Sequence
<220> FEATURE:
<223> OTHER INFORMATION: reverse primer for pT-YlOCH1+

<400> SEQUENCE: 9
ccatggatcc gtagatctag gagttcgaag acgttg                               36

<210> SEQ ID NO 10
<211> LENGTH: 36
<212> TYPE: DNA
<213> ORGANISM: Artificial Sequence
<220> FEATURE:
<223> OTHER INFORMATION: forward primer for pT-YlOCH1+

<400> SEQUENCE: 10
agatctacgg atccatggga ccgactctgt cttcga                               36

<210> SEQ ID NO 11
<211> LENGTH: 18
<212> TYPE: DNA
<213> ORGANISM: Artificial Sequence
<220> FEATURE:
<223> OTHER INFORMATION: reverse primer for pT-YlOCH1+

<400> SEQUENCE: 11
catcctcctg atatacgc                                                  18

<210> SEQ ID NO 12
<211> LENGTH: 299
<212> TYPE: PRT
<213> ORGANISM: Aspergillus fumigates
<220> FEATURE:
<223> OTHER INFORMATION: AfMnn4p

<400> SEQUENCE: 12

Met Ile Pro Arg Ile Leu Arg Leu Ile Val Leu Ala Ile Trp Ser Ala
1               5                   10                  15

Glu Ala Val Ala Ser Pro Val Arg Ser Ser Asp Gln Asp His Ser Asn
                20                  25                  30

Val Asn His Gly Lys Ile Leu Thr His Glu Pro Glu Tyr Asp Pro Leu
            35                  40                  45

Trp Glu Lys Tyr Gly Leu Asn Lys Ser Gln Glu Phe Lys Tyr Phe His
        50                  55                  60
```

```
Glu Pro Gly Asn Asp Asp Ile Leu Gly His Tyr Asp Thr Arg Phe Phe
 65                  70                  75                  80

Thr Glu Pro Val Pro Asp Lys Glu Arg Ser Glu Thr Met Thr His Met
                 85                  90                  95

Ile Arg Ala Tyr Leu Asn Phe Phe Asn Glu Arg Gly Leu Glu Thr Trp
            100                 105                 110

Ile Ala His Gly Thr Leu Leu Gly Trp Trp Asn Gly Lys Val Leu
            115                 120                 125

Pro Trp Trp Asp Ile Asp Thr Gln Val Leu Asp Thr Thr Leu Leu Arg
130                 135                 140

Leu Ala Asp Gln Phe Asn Gln Thr Val Val His Tyr Thr Ala Ala Asp
145                 150                 155                 160

Ser Ser Val Glu Arg Ser Tyr Leu Leu Asp Val Asn Pro Trp Ala Arg
                165                 170                 175

Gln Arg Glu Arg Gly Gln Gly Leu Asn Ile Ile Asp Ala Arg Trp Ile
            180                 185                 190

Asp Arg Arg Thr Gly Leu Tyr Ile Asp Ile Thr Gly Leu Ser Arg Leu
            195                 200                 205

Glu Pro Glu Lys Pro Ser Leu Trp Gln Asp Lys Asn Asp His Lys Tyr
210                 215                 220

Gln Thr Gly Asp Ile Tyr Pro Leu Arg Lys Thr Thr Phe Glu Gly Val
225                 230                 235                 240

Pro Ala Lys Ile Pro Phe Asp Tyr Asp Ser Val Leu Ile Lys Glu Tyr
                245                 250                 255

Thr Gln Glu Ala Leu Thr Ser Thr Lys Phe His Asn His Thr Trp Tyr
            260                 265                 270

Pro Asp Leu Glu Gln Trp Val Ser Asp His Asp Glu Ile Ala Lys Gly
            275                 280                 285

Lys Leu Asn Asp Asp Arg Gln Tyr Glu Arg Arg
290                 295

<210> SEQ ID NO 13
<211> LENGTH: 997
<212> TYPE: PRT
<213> ORGANISM: Candida albicans
<220> FEATURE:
<223> OTHER INFORMATION: CaMnn4p

<400> SEQUENCE: 13

Met Ser Asn Thr Ile Pro Gln Tyr Phe Ile Arg Ile Phe Asn Leu Ile
  1               5                  10                  15

Phe Ser Ala Arg Arg Lys Asn Phe Gln Leu Ala Leu Ile Ser Gly Leu
                 20                  25                  30

Leu Phe Phe Gly Ser Phe Ala Ile Leu Ser Thr Thr Ser Tyr Ser Lys
             35                  40                  45

Lys Phe Asn Tyr Phe Asp Asp Leu Ile Leu Lys Ile Tyr Asp Tyr Asn
 50                  55                  60

Tyr Leu Thr Asn Asn Tyr Asn Ile Asp Tyr Leu Ala Lys Asn Asp Pro
 65                  70                  75                  80

Glu Ala Tyr Phe Asn Val Lys Val Gln Gln Ile Val Asp Glu Lys Lys
                 85                  90                  95

Gln His Asp Leu Glu Ser Lys Phe Trp Ser Leu Asp Thr Lys Ile Asn
            100                 105                 110

Asp Asp Gln Ala Thr Leu Gln Ile Pro Ala Tyr Phe Thr Tyr Asn Lys
            115                 120                 125
```

-continued

```
Pro Arg Asp Asn Lys Asn Leu Glu Asp Ser Glu Gln Ser Ser Lys Pro
    130                 135                 140
Val Glu Lys Pro Leu Ile Gln Pro Phe Asp Pro Arg Phe Thr Leu Ala
145                 150                 155                 160
Met Tyr Tyr Tyr Tyr Leu Asp Gln Gln Met Thr Thr Ala His His Asp
                165                 170                 175
Ser Ser Ser Ser Ser Ser Gly Asn Ser Ile Thr Val Pro Phe Asn Trp
                180                 185                 190
Tyr Asp Trp Val Asp Met Ser Val Leu Asn Lys Tyr Leu Leu Ala Pro
            195                 200                 205
Asn Lys Asp Lys Pro Asp Cys Ser Ile Leu Asp Ala His Glu Asp Ala
    210                 215                 220
Arg Lys Ile Glu Thr Glu Lys Lys Met Glu Lys Leu Ala Lys Gln
225                 230                 235                 240
Trp Asp Glu Asn Lys Arg Lys Ala Glu Glu Lys Lys Ala Glu
                245                 250                 255
Glu Asp Lys Lys Lys Glu Glu Glu Lys Lys Ala Glu Glu Glu
                260                 265                 270
Glu Lys Gln Arg His Glu Gln Glu Lys Gln Ala Leu Glu Glu Asp Lys
            275                 280                 285
Lys Lys Leu Glu Glu Lys Lys Ile Glu Glu Lys Asn Lys
    290                 295                 300
Leu Gln Glu Gln Gln Gln Gln Gln Glu Gly Lys Ala Asn Asp
305                 310                 315                 320
Gly Asn Gln Glu His Ser Lys Phe Val Lys Arg Asp Asp Glu Ile Lys
                325                 330                 335
Met Ser Thr Ser Gln Asp Lys Ser Asp Ser Asp Ala Asp Arg Ala Lys
                340                 345                 350
Ile Asp Met Thr Thr Phe Phe Asn Glu Ala Phe Glu Lys Leu Ser Asp
            355                 360                 365
Glu Asp Lys Ala Ser Val Ala Lys Asp Val Glu Asp Ala Val Lys Lys
    370                 375                 380
Ile Thr Gln Pro Ser Ser Trp Cys Val Pro Asn Ala Lys Leu Ser Ile
385                 390                 395                 400
Asp His Ser Asp Lys Gln Ile Val His Pro Gly Phe Asn Val Phe Lys
                405                 410                 415
Ser Pro Gly Arg Thr Pro Gln Lys Ala Ile Ile Ala Gly Lys Ser
                420                 425                 430
Phe Leu Tyr Ser Tyr Ala Pro Pro Ser Ser Ile Leu Phe Leu Thr
            435                 440                 445
Ser Glu Gly Ser Tyr Ser Val Asn Val Gln His Ser Ala Pro Leu Leu
    450                 455                 460
Arg Asn Gly Ile Pro Glu Ser Tyr Leu Ala Asn Asn Phe Asp Val
465                 470                 475                 480
Ser Leu Asn Val Leu Gln Gln Leu His Lys Leu Lys Asn His Lys
                485                 490                 495
Pro Asp Thr Ala Lys Val Ile Asn Asp Tyr Leu Leu His Ile Pro Lys
                500                 505                 510
Glu Ser Phe Lys Tyr Asp Pro Asp Ser Ile Ile Phe Asp Tyr Thr Lys
            515                 520                 525
Arg Leu Asp Lys Gly Glu Lys Leu Thr Ile Lys Glu Leu Lys Tyr Leu
    530                 535                 540
Gln Ser Leu Glu Tyr Ser Lys Asp Lys Val Ala His Gly Gly Pro Pro
545                 550                 555                 560
```

```
Lys Tyr Phe Ala Glu Ser Arg Leu Ile Gly Thr Thr Val Gly Asp His
                565                 570                 575
Tyr Asp Trp Arg Phe Phe Asn Gly Val Gln Phe Gly Thr Val Asp Gln
                580                 585                 590
Ser Leu Thr Leu His Arg Leu Ile Arg Thr Trp Leu Ser Phe Thr Arg
                595                 600                 605
Lys Ser Gly Ile Thr Thr Trp Ile Ala His Gly Ser Leu Leu Ser Trp
                610                 615                 620
Tyr Trp Asn Gly Met Ala Phe Pro Trp Asp Asn Ile Asp Val Gln
625                 630                 635                 640
Val Pro Ile Met Asp Leu His Lys Leu Ser Leu Gln Phe Asn Gln Thr
                645                 650                 655
Ile Val Val Glu Asp Pro Glu Asp Gly Phe Gly Arg Tyr Phe Leu Asp
                660                 665                 670
Ile Gly Ser Phe Ile Thr Leu Arg Glu Lys Gly Asn Gly Asn Asn Asn
                675                 680                 685
Ile Asp Ala Arg Phe Ile Asp Ile Asp Thr Gly Leu Tyr Ile Asp Ile
                690                 695                 700
Thr Ala Leu Ala Leu Ser Asn Ser Glu Thr Pro Lys Ser Asp Leu Ala
705                 710                 715                 720
Glu Leu Pro Lys Asn Phe Glu Ile Lys Asp Asn Asn Tyr Lys Pro Ala
                725                 730                 735
Asn Glu Leu Leu Gln Ile Tyr Asn Cys Arg Asn Asn His Phe Asn Ser
                740                 745                 750
Tyr Asp Glu Leu Ser Pro Leu Met Lys Ser Ser Val Glu Gly Glu Ile
                755                 760                 765
Gly Tyr Ile Pro Ser Arg Tyr Ser Thr Ile Leu Thr Arg Glu Tyr Arg
                770                 775                 780
Ser Gly Leu Ser Ser Asn Ser His Gly Gly Tyr Ile Phe Ile Ala Lys
785                 790                 795                 800
Leu Arg Leu Trp Val Lys Glu Asp Leu Tyr Tyr Phe Ile Lys His
                805                 810                 815
Arg Asp Gln Trp Thr Lys Tyr His Ser Phe Asn Thr Lys Leu Ser Gln
                820                 825                 830
Asp Pro Ser Asn Thr Leu Leu Gln Asp Tyr Ser Tyr Leu Met Ser Glu
                835                 840                 845
Gln Glu Tyr Glu Asn Leu Gln Tyr Ser Thr Asp Leu Glu His Asp Asn
                850                 855                 860
Pro Phe Lys Lys Thr Lys Lys Pro Leu Glu Leu Lys Asn Ser Glu Leu
865                 870                 875                 880
Glu Lys Leu Lys His Met Asn Glu Ser Glu Leu Leu Gln Phe Leu Asn
                885                 890                 895
Asn Asp Asp Ile Leu Ile Gln Phe Phe Asn Ala Lys Glu Phe Thr Ser
                900                 905                 910
Phe His Glu Ser Glu Ile Met Gln Leu Thr Phe Gly Lys Ser Thr Ala
                915                 920                 925
Lys Leu Met Ser Ser Ala Ile Asp Phe Pro Pro Ile Lys Tyr Glu Pro
                930                 935                 940
Tyr Leu Tyr Lys Leu Asn His Asp Leu Asp Thr Phe Glu Asn Lys Val
945                 950                 955                 960
Asp Arg Tyr Leu Ala Leu Gln Asp Ala Tyr Gln Gln Glu His Asn Asn
                965                 970                 975
Ser Pro Ser Gly Gly Ser Asp Asn Gly Phe Met Glu Ile Glu Glu Asp
```

```
                980              985              990
Leu Asp Phe Ala Phe
        995

<210> SEQ ID NO 14
<211> LENGTH: 860
<212> TYPE: PRT
<213> ORGANISM: Pichia pastoris
<220> FEATURE:
<223> OTHER INFORMATION: PpMnn4Ap

<400> SEQUENCE: 14

Met Lys Val Ser Lys Arg Leu Ile Pro Arg Ser Arg Leu Leu Ile
1               5                   10                  15

Met Met Met Leu Leu Val Val Tyr Gln Leu Val Val Leu Val Leu Gly
            20                  25                  30

Leu Glu Ser Val Ser Glu Gly Lys Leu Ala Ser Leu Leu Asp Leu Gly
        35                  40                  45

Asp Trp Asp Leu Ala Asn Ser Ser Leu Ser Ile Ser Asp Phe Ile Lys
    50                  55                  60

Leu Lys Leu Lys Gly Gln Lys Thr Tyr His Lys Phe Asp Glu His Val
65                  70                  75                  80

Phe Ala Ala Met Ala Arg Ile Gln Ser Asn Glu Asn Gly Lys Leu Ala
                85                  90                  95

Asp Tyr Glu Ser Thr Ser Ser Lys Thr Asp Val Thr Ile Gln Asn Val
            100                 105                 110

Glu Leu Trp Lys Arg Leu Ser Glu Glu Tyr Thr Tyr Glu Pro Arg
        115                 120                 125

Ile Thr Leu Ala Val Tyr Leu Ser Tyr Ile His Gln Arg Thr Tyr Asp
    130                 135                 140

Arg Tyr Ala Thr Ser Tyr Ala Pro Tyr Asn Leu Arg Val Pro Phe Ser
145                 150                 155                 160

Trp Ala Asp Trp Ile Asp Leu Thr Ala Leu Asn Gln Tyr Leu Asp Lys
                165                 170                 175

Thr Lys Gly Cys Glu Ala Val Phe Pro Arg Glu Ser Glu Ala Thr Met
            180                 185                 190

Lys Leu Asn Asn Ile Thr Val Val Asp Trp Leu Glu Gly Leu Cys Ile
        195                 200                 205

Thr Asp Lys Ser Leu Gln Asn Ser Val Asn Ser Thr Tyr Ala Glu Glu
    210                 215                 220

Ile Asn Ser Arg Asp Ile Leu Ser Pro Asn Phe His Val Phe Gly Tyr
225                 230                 235                 240

Ser Asp Ala Lys Asp Asn Pro Gln Gln Lys Ile Phe Gln Ser Lys Ser
                245                 250                 255

Tyr Ile Asn Ser Lys Leu Pro Leu Pro Lys Ser Leu Ile Phe Leu Thr
            260                 265                 270

Asp Gly Gly Ser Tyr Ala Leu Thr Val Asp Arg Thr Gln Asn Lys Arg
        275                 280                 285

Ile Leu Lys Ser Gly Leu Leu Ser His Phe Ser Lys Lys Lys
    290                 295                 300

Glu His Asn Leu Pro Gln Asp Gln Lys Thr Phe Thr Phe Asp Pro Val
305                 310                 315                 320

Tyr Glu Phe Asn Arg Leu Lys Ser Gln Val Lys Pro Arg Pro Ile Ser
                325                 330                 335

Ser Glu Pro Ser Ile Asp Ser Ala Leu Lys Glu Asn Asp Tyr Lys Leu
            340                 345                 350
```

```
Lys Leu Lys Glu Ser Ser Phe Ile Phe Asn Tyr Gly Arg Ile Leu Ser
            355                 360                 365

Asn Tyr Glu Glu Arg Leu Glu Ser Leu Asn Asp Phe Glu Lys Ser His
    370                 375                 380

Tyr Glu Ser Leu Ala Tyr Ser Ser Leu Leu Glu Ala Arg Lys Leu Pro
385                 390                 395                 400

Lys Tyr Phe Gly Glu Val Ile Leu Lys Asn Pro Gln Asp Gly Gly Ile
                405                 410                 415

His Tyr Asp Tyr Arg Phe Phe Ser Gly Leu Ile Asp Lys Thr Gln Ile
                420                 425                 430

Asn His Phe Glu Asp Glu Thr Glu Arg Lys Lys Ile Ile Met Arg Arg
            435                 440                 445

Leu Leu Arg Thr Trp Gln Tyr Phe Thr Tyr His Asn Asn Ile Ile Asn
        450                 455                 460

Trp Ile Ser His Gly Ser Leu Leu Ser Trp Tyr Trp Asp Gly Leu Ser
465                 470                 475                 480

Phe Pro Trp Asp Asn Asp Ile Asp Val Gln Met Pro Ile Met Glu Leu
                485                 490                 495

Asn Asn Phe Cys Lys Gln Phe Asn Asn Ser Leu Val Val Glu Asp Val
            500                 505                 510

Ser Gln Gly Phe Gly Arg Tyr Tyr Val Asp Cys Thr Ser Phe Leu Ala
        515                 520                 525

Gln Arg Thr Arg Gly Asn Gly Asn Asn Asn Ile Asp Ala Arg Phe Ile
    530                 535                 540

Asp Val Ser Ser Gly Leu Phe Ile Asp Ile Thr Gly Leu Ala Leu Thr
545                 550                 555                 560

Gly Ser Thr Met Pro Lys Arg Tyr Ser Asn Lys Leu Ile Lys Gln Pro
                565                 570                 575

Lys Lys Ser Thr Asp Ser Thr Gly Ser Thr Pro Glu Asn Gly Leu Thr
            580                 585                 590

Arg Asn Leu Arg Gln Asn Leu Asn Ala Gln Val Tyr Asn Cys Arg Asn
        595                 600                 605

Gly His Phe Tyr Gln Tyr Ser Glu Leu Ser Pro Leu Lys Leu Ser Ile
    610                 615                 620

Val Glu Gly Ala Leu Thr Leu Ile Pro Asn Asp Phe Val Thr Ile Leu
625                 630                 635                 640

Glu Thr Glu Tyr Gln Arg Arg Gly Leu Glu Lys Asn Thr Tyr Ala Lys
                645                 650                 655

Tyr Leu Tyr Val Pro Glu Leu Arg Leu Trp Met Ser Tyr Asn Asp Ile
            660                 665                 670

Tyr Asp Ile Leu Gln Gly Thr Asn Ser His Gly Arg Pro Leu Ser Ala
        675                 680                 685

Lys Thr Met Ala Thr Ile Phe Pro Arg Leu Asn Ser Asp Ile Asn Leu
    690                 695                 700

Lys Lys Phe Leu Arg Asn Asp His Thr Phe Lys Asn Ile Tyr Ser Thr
705                 710                 715                 720

Phe Asn Val Thr Arg Val His Glu Glu Glu Leu Lys His Leu Ile Val
                725                 730                 735

Asn Tyr Asp Gln Asn Lys Arg Lys Ser Ala Glu Tyr Arg Gln Phe Leu
            740                 745                 750

Glu Asn Leu Arg Phe Met Asn Pro Ile Arg Lys Asp Leu Val Thr Tyr
        755                 760                 765

Glu Ser Arg Leu Lys Ala Leu Asp Gly Tyr Asn Glu Val Glu Glu Leu
```

```
                    770                 775                 780
Glu Lys Lys Gln Glu Asn Arg Glu Lys Glu Arg Lys Glu Lys Glu
785                 790                 795                 800

Lys Glu Glu Lys Glu Lys Lys Glu Lys Glu Glu Lys Glu Lys Glu
                    805                 810                 815

Lys Glu Glu Lys Glu Lys Lys Glu Lys Glu Glu Lys Glu Arg Lys Glu
                    820                 825                 830

Lys Glu Glu Lys Glu Glu Tyr Glu Glu Asp Asp Asn Glu Gly Glu Gln
                    835                 840                 845

Pro Thr Glu Gln Lys Ser Gln Gln Glu Ala Lys Glu
                    850                 855                 860

<210> SEQ ID NO 15
<211> LENGTH: 641
<212> TYPE: PRT
<213> ORGANISM: Pichia pastoris
<220> FEATURE:
<223> OTHER INFORMATION: PpMnn4Bp

<400> SEQUENCE: 15

Met Phe Lys Glu Thr Ser Lys Asn Leu Phe Ser Ile Asn Thr Phe Asn
1               5                   10                  15

Thr Val Glu Tyr Met Tyr Met Met Leu Leu Leu Thr Ala Tyr Leu Asn
                20                  25                  30

His Leu Leu His Ser Leu Asp Asn Asn His Leu Val Glu Ser Asp Val
            35                  40                  45

Asn Tyr Leu Leu Gln Arg Val Thr Asn Lys Val Lys Phe Asp Glu Glu
    50                  55                  60

Ala Val Leu Pro Phe Ala Asn Leu Asn Arg Arg Thr Glu Arg Phe Asp
65              70                  75                  80

Arg Leu Pro Val Ala Ala Tyr Leu Arg Ser Gln Asp Gln Tyr Ser Glu
                85                  90                  95

Leu Pro Gln Gly Asp Leu Asn Asp Ile Pro Pro Leu Glu Val Ser Phe
            100                 105                 110

His Trp Asp Asp Trp Leu Ser Leu Gly Ile Ala Ser Thr Phe Trp Asp
        115                 120                 125

Ala Phe Asp Asn Tyr Asn Lys Arg Gln Gly Glu Asn Ala Ile Ser Tyr
    130                 135                 140

Glu Gln Leu Gln Ala Ile Leu Val Asn Asp Leu Glu Asp Phe Ser Pro
145                 150                 155                 160

Tyr Thr Ala His Ile Leu His Ser Asn Val Glu Val Tyr Lys Tyr Arg
                165                 170                 175

Thr Ile Pro Gln Ile Val Tyr Met Ser Asn Lys Gly Tyr Phe Glu Leu
            180                 185                 190

Leu Val Thr Glu Lys Glu Lys Leu Ser Asn Glu Gly Leu Trp Ser Ile
        195                 200                 205

Phe His Gln Lys Gln Gly Gly Leu Asn Glu Phe Ser Ser Leu Asn Leu
    210                 215                 220

Ile Glu Glu Val Asp Ala Leu Asp Glu Ile Tyr Asp Ser Lys Gly Leu
225                 230                 235                 240

Pro Ala Trp Asp Pro Pro Phe Pro Glu Glu Leu Asp Ala Ser Asp Glu
                245                 250                 255

Asp Phe Lys Phe Asn Ala Thr Glu Glu Leu Ala Lys Val Glu Gln Ile
            260                 265                 270

Lys Glu Pro Lys Leu Glu Asp Ile Phe Tyr Gln Glu Gly Leu Gln His
        275                 280                 285
```

Gly Ile Gln Thr Leu Pro Ser Asp Ala Ser Val Tyr Phe Pro Val Asn
            290                 295                 300

Tyr Val Glu Asn Asp Pro Gly Leu Gln Ser His His Leu His Phe Pro
305                 310                 315                 320

Phe Phe Ser Gly Met Val Leu Pro Arg Glu Ile His Ser Val His
                325                 330                 335

His Met Asn Lys Ala Phe Phe Leu Phe Ala Arg Gln His Gly Tyr Val
            340                 345                 350

Val Trp Phe Phe Tyr Gly Asn Leu Ile Gly Trp Tyr Tyr Asn Gly Asn
        355                 360                 365

Asn His Pro Trp Asp Ser Asp Ile Asp Ala Ile Met Pro Met Ala Glu
    370                 375                 380

Met Ala Arg Met Ala His His Asn Asn Thr Leu Ile Ile Glu Asn
385                 390                 395                 400

Pro His Asp Gly Tyr Gly Thr Tyr Leu Leu Thr Ile Ser Pro Trp Phe
                405                 410                 415

Thr Lys Lys Thr Arg Gly Gly Asn His Ile Asp Gly Arg Phe Val Asp
            420                 425                 430

Val Lys Arg Gly Thr Tyr Ile Asp Leu Ser Ala Ile Ser Ala Met His
        435                 440                 445

Gly Ile Tyr Pro Asp Trp Val Arg Asp Gly Val Lys Glu Asn Pro Lys
    450                 455                 460

Asn Leu Ala Leu Ala Asp Lys Asn Gly Asn Trp Tyr Leu Thr Arg Asp
465                 470                 475                 480

Ile Leu Pro Leu Arg Arg Thr Ile Phe Glu Gly Ser Arg Ser Tyr Thr
                485                 490                 495

Val Lys Asp Ile Glu Asp Thr Leu Leu Arg Asn Tyr Gly Asp Lys Val
            500                 505                 510

Leu Ile Asn Thr Glu Leu Ala Asp His Glu Trp His Asp Asp Trp Lys
        515                 520                 525

Met Trp Val Gln Lys Lys Lys Tyr Cys Thr Tyr Glu Glu Phe Glu Asp
    530                 535                 540

Tyr Leu Ser Ala His Gly Gly Val Glu Tyr Asp Glu Asp Gly Val Leu
545                 550                 555                 560

Thr Leu Glu Gly Ala Cys Gly Phe Glu Glu Val Arg Gln Asp Trp Ile
                565                 570                 575

Ile Thr Arg Glu Ser Val Asn Leu His Met Lys Glu Trp Glu Ala Ile
            580                 585                 590

Gln Arg Asn Glu Ser Thr Thr Glu Tyr Thr Ala Lys Asp Leu Pro Arg
        595                 600                 605

Tyr Arg Pro Asp Ser Phe Lys Asn Leu Leu Asp Gly Val Ser Asn His
    610                 615                 620

Gly Asn Gly Asn Val Gly Lys Ile Glu His Val Lys Leu Glu His Asn
625                 630                 635                 640

Asp

<210> SEQ ID NO 16
<211> LENGTH: 718
<212> TYPE: PRT
<213> ORGANISM: Pichia pastoris
<220> FEATURE:
<223> OTHER INFORMATION: PpMnn4Cp

<400> SEQUENCE: 16

Met Ser Gly Asn Pro Phe Leu Phe Ser Pro Ser Asn Phe Asp Phe Ser

-continued

```
1               5               10              15
Gly Leu Asp His Tyr Arg Ser Thr Asp Lys Asp His Leu Ala Leu Asp
                20                  25                  30

Val Leu Asp Tyr Asp Lys Asn His Phe Phe Ser Arg Asn Ser Pro Ser
                35                  40                  45

Leu Lys Ser Arg Ile His Phe Tyr Arg His Lys Leu Thr Thr Arg Lys
                50                  55                  60

Gln Ile Gly Leu Phe Ser Gly Arg Leu Lys Leu Phe Val Leu Ala Leu
65                  70                  75                  80

Phe Val Leu Ile Thr Phe Ser Ala Ile His Ile Pro Ile Pro Phe Ser
                85                  90                  95

Leu Asp Ile Leu Gly Ser His Val Lys Tyr Leu Pro Leu Arg Glu Lys
                100                 105                 110

Val Asp Pro Glu Glu Ala Leu His His Gly Leu Asp Leu Ser Val Ala
                115                 120                 125

Glu Leu Pro Phe Phe Asn Asp Asp Met Met Ser Glu Phe Asn Tyr Asp
                130                 135                 140

Pro Arg Leu Pro Thr Ala Leu Ile Leu Lys Leu Val Leu Asp His Ile
145                 150                 155                 160

Ser Val Arg Asn Gly Thr Phe Asp Ala Lys Phe Lys Val Pro Phe Asn
                165                 170                 175

Trp Lys Leu Val Asp Leu His Ser Arg Leu Val Pro Ser Asn Ser Trp
                180                 185                 190

Tyr Asn Arg Phe Arg Leu Pro Ser Gly Arg Phe Glu Thr Cys Asp Glu
                195                 200                 205

Phe Lys Arg Phe Phe Gly Ile Thr Lys Asn His Phe Gly Thr Asp Leu
                210                 215                 220

Asp Asn Cys Val Asp Ile Glu Tyr Asp Thr Pro Gly Gly Tyr Pro Lys
225                 230                 235                 240

Phe Lys Val Leu His Ala Glu Asp Lys Ala Leu Pro Tyr Glu Ala Arg
                245                 250                 255

Ile Ile Tyr Gly Ala Ser Tyr Leu Tyr His Glu Ala Gln Asn Pro Lys
                260                 265                 270

Arg Leu Ile Phe Leu Gly Leu Gly Lys Ser Asn Glu Ser Leu Ile Leu
                275                 280                 285

Pro Val Glu Ala Asn Asp Ser Ser Asn Leu Met Gln Phe Asn His Glu
                290                 295                 300

Tyr Ala Arg Ser Phe Asn Asp Gln Pro Phe Val Ser Leu Glu Glu Leu
305                 310                 315                 320

Val Lys Lys Val Ser Leu Thr Leu Asn Leu Asn Ser Asp Lys Val Leu
                325                 330                 335

Pro Ile Asn Glu Leu Asp Val Ile Lys Asp Thr Pro Arg Leu Met Asn
                340                 345                 350

His Asn Asn Gln Gly Leu Ser Ile Asp Lys Ser Ser Phe Gln Trp Asp
                355                 360                 365

Leu Glu Arg Glu Leu Gln Leu Leu Glu His Arg Thr Ser Gln Val Asn
370                 375                 380

Asp Val Glu Gly Leu Asp Ala Gly Ile Tyr Ser Thr Ile Gln Cys Glu
385                 390                 395                 400

Met Arg Ser Met Tyr Asp Phe Ser Lys Tyr Phe His Glu Ser Lys Val
                405                 410                 415

Ser Gly Lys Tyr Leu Pro Ser Gly Glu His Tyr Asp Trp Arg Phe Phe
                420                 425                 430
```

-continued

Asn Gly Phe Tyr Leu Ser Gln Gln Glu Asn Leu Ala Val Leu His Arg
            435                 440                 445

Leu Gly Arg Ala Trp Leu Arg Phe Ser Arg Ala Ala Gly Leu His Thr
450                 455                 460

Trp Ile Ala His Gly Thr Leu Leu Gly Trp Tyr Trp Asn Gly Leu Ile
465                 470                 475                 480

Leu Pro Trp Asp Gln Asp Leu Asp Val Gln Met Thr Val Gln Ser Leu
                485                 490                 495

Tyr Leu Leu Gly Arg Asn Phe Asn Ser Ser Leu Val Thr Asp Val Ser
                500                 505                 510

Ile Glu Asp Gly Tyr Ser Ser Ala Leu Gly His Tyr Tyr Ile Asp Val
            515                 520                 525

Gly Ser Ser Phe Phe Val Arg Asp Lys Leu Asn Gly Asn Asn Ala Ile
530                 535                 540

Asp Ala Arg Phe Val Asp Thr Glu Thr Gly Leu Tyr Val Asp Ile Thr
545                 550                 555                 560

Ala Leu Ala Phe Thr Asp His Leu Lys Leu Lys Leu Thr Thr Lys Glu
                565                 570                 575

Lys Val Glu Leu Gln Lys Val Met Asp Pro Asn Val Lys Glu Lys Leu
            580                 585                 590

Gln Trp Ile Lys Asn Lys Tyr Ser Thr Ala Thr Leu Pro Gly Val Ile
            595                 600                 605

Glu Thr Asp Arg Asn Lys Val Ser Asp Ala Leu Glu Lys Gln Phe His
610                 615                 620

Asp Phe Lys Phe Asp Asn Phe Val Asn Lys Leu Phe His Cys Arg
625                 630                 635                 640

Asn Asn His Phe Tyr Lys Tyr Gly Glu Val Gly Arg Leu Arg Ser Thr
                645                 650                 655

Met Phe Glu Gly Val Pro Ala Leu Ile Pro Phe Glu Phe Glu Ser Ile
                660                 665                 670

Leu Lys Arg Glu Tyr Pro Lys Gly Leu Thr Leu Lys His Phe Ser Asn
            675                 680                 685

His Phe Trp Asp Pro Val Asn Arg Leu Trp Val Pro Glu Lys Lys Lys
            690                 695                 700

Lys Ile Arg His Ile Glu Phe Ser Leu Thr Lys Glu Val Thr
705                 710                 715

<210> SEQ ID NO 17
<211> LENGTH: 345
<212> TYPE: PRT
<213> ORGANISM: Neurospora crassa
<220> FEATURE:
<223> OTHER INFORMATION: NcMnn4p

<400> SEQUENCE: 17

Met Trp Ser Ser Leu Thr Pro Ala Arg Arg Gln Ala Thr Thr Thr Ser
1               5                   10                  15

Trp Arg Asp Arg Leu Leu Thr Leu Leu Met Ala Leu Thr Phe Val Leu
            20                  25                  30

Ser Ser Leu Ala Ser Pro Leu Pro Ile Glu Gly Ala Val Val Lys Ala
        35                  40                  45

Asn Asn Asn Asp Ala Val Ser Gln Pro Ala Gln Ala Gln Ala Lys
    50                  55                  60

Ala Glu Val Arg Gln Phe Ser Ala Pro Ala Gln Ala Glu Ala Glu
65                  70                  75                  80

Pro Ala Thr Ala Thr Thr Ser Asp Asp Thr Thr Asn Thr Asn Thr Asp

```
                   85                  90                  95
Asp Asp Asp Pro Leu Leu Pro Glu Arg Lys Tyr Phe His Glu Pro Gly
            100                 105                 110

Trp Thr Glu Glu Leu Ser His Tyr Thr Arg Phe Phe Thr Ser Pro Val
            115                 120                 125

Pro Tyr Asp Pro His Leu Val His Leu Arg His Leu Ile Arg Ser Tyr
            130                 135                 140

Leu Leu Met Thr Ser Ser Arg Ser Leu Thr Thr Trp Leu Ala His Gly
145                 150                 155                 160

Thr Leu Leu Gly Trp Tyr Trp Asn Gly Ala Ile Met Pro Trp Asp Tyr
                165                 170                 175

Asp Leu Asp Val Gln Val Ser Asn Ile Thr Leu Gly Gln Met Ala Arg
            180                 185                 190

Asp Trp Asn Gln Thr Thr Phe Asp Tyr Val Tyr Thr Leu Ser Glu Glu
            195                 200                 205

Glu Glu Lys Glu Gly Leu Gly Lys Gln Gly Glu Val Thr Val Lys Lys
            210                 215                 220

Tyr Leu Leu Asp Val Asn Pro Tyr Trp Ala Gln Arg Thr Arg Leu Glu
225                 230                 235                 240

Gly Met Asn Val Ile Asp Ala Arg Trp Ile Asp Met Glu Asn Gly Met
                245                 250                 255

Tyr Val Asp Ile Thr Gly Leu Ser Glu Asp Arg Glu Glu Thr Gly Thr
            260                 265                 270

Arg Gln Gly Val Trp Ser Asp Lys Asn Tyr His Gly Tyr Gly Thr Arg
            275                 280                 285

Gln Ile Trp Pro Leu Arg Arg Thr Glu Phe Glu Gly Val Glu Ala Trp
            290                 295                 300

Val Pro Trp Asp Val Glu Glu Ile Leu Lys Glu Glu Tyr Gly Val Lys
305                 310                 315                 320

Ser Leu Thr Glu Glu Ser Phe Ala Gly His Gln Phe Asp His Gly Arg
                325                 330                 335

Lys Gln Trp Val Lys Thr Glu Leu Ala
            340                 345

<210> SEQ ID NO 18
<211> LENGTH: 777
<212> TYPE: PRT
<213> ORGANISM: Pichia pastoris
<220> FEATURE:
<223> OTHER INFORMATION: PpPno1p

<400> SEQUENCE: 18

Met Thr Leu Arg Ser Ala Ile Lys Ala Arg Thr Ser Lys Gly Leu Ile
1               5                   10                  15

Gly Ala Val Ile Ile Ala Ser Ile Ile Phe Thr Thr Val Thr Phe
            20                  25                  30

Tyr Asp Glu Ser Lys Ile Val Gly Ile Arg Val Ser Asp Thr Tyr
            35                  40                  45

Thr Gly His Ser Ala Val Ser Thr Phe Asn Ala Ser Ser Val Val
        50                  55                  60

Ser Asp Asn Lys Ile Asn Gly Tyr Gly Leu Pro Leu Ile Asp Thr Glu
65              70                  75                  80

Ser Asn Ser Arg Tyr Glu Asp Pro Asp Ile Ser Ile Glu Asn Glu
                85                  90                  95

Leu Arg Tyr Arg Ile Ala Gln Ser Thr Lys Glu Glu Asn Met Trp
            100                 105                 110
```

```
Lys Leu Asp Thr Thr Leu Thr Glu Ala Ser Leu Lys Ile Pro Asn Ile
            115                 120                 125
Gln Ser Phe Glu Leu Gln Pro Phe Lys Glu Arg Leu Asp Asn Ser Leu
        130                 135                 140
Tyr Asn Ser Lys Asn Ile Gly Asn Phe Tyr Tyr Asp Pro Arg Leu
145                 150                 155                 160
Thr Phe Ser Val Tyr Leu Lys Tyr Ile Lys Asp Lys Leu Ala Ser Gly
                165                 170                 175
Ser Thr Thr Asn Leu Thr Ile Pro Phe Asn Trp Ala His Phe Arg Asp
            180                 185                 190
Leu Ser Ser Leu Asn Pro Tyr Leu Asp Ile Lys Gln Glu Asp Lys Val
        195                 200                 205
Ala Cys Asp Tyr Phe Tyr Glu Ser Ser Asn Lys Asp Lys Arg Lys Pro
    210                 215                 220
Thr Gly Asn Cys Ile Glu Phe Lys Asp Val Arg Asp Glu His Leu Ile
225                 230                 235                 240
Gln Tyr Gly Ile Ser Ser Lys Asp His Leu Pro Gly Pro Phe Ile Leu
                245                 250                 255
Lys Ser Leu Gly Ile Pro Met Gln His Thr Ala Lys Arg Leu Glu Ser
            260                 265                 270
Asn Leu Tyr Leu Leu Thr Gly Ala Pro Val Pro Leu Ser Leu Ser Phe
        275                 280                 285
Met Thr Lys Lys Gly Leu Tyr Gln Val Gly Val Asp Gln Thr Gly Lys
    290                 295                 300
Leu Asp Pro Asn Ile Ala Arg Thr Glu Leu Trp Glu Phe Tyr Lys Asn
305                 310                 315                 320
Gly Lys Glu Asn Leu Gln Phe Asn Ala Gln Glu Leu Ser His Leu
                325                 330                 335
Ile Glu Thr Val Pro Ser Ser Ser Asn Ser Ser Gly Glu Gly Tyr
            340                 345                 350
Phe Thr Thr Glu Leu Lys Glu Asn Asn Phe Glu Leu Pro Leu Ser Lys
        355                 360                 365
Asn Asp Phe Thr Phe Asp Asp Ser Glu Val Glu Ser Leu Ile Lys Gly
    370                 375                 380
Leu Ser Glu Gln Asp Leu Asp Leu His Thr Gln Arg Tyr Lys Glu Ser
385                 390                 395                 400
Leu Gln Tyr Ser Phe Ala Thr Arg Glu Asn Asp Val Lys Lys Tyr Phe
                405                 410                 415
Tyr Glu Ala Arg Met Ile Ile Asn Thr Val Asn Lys Glu Gly Gly Ala
            420                 425                 430
His Tyr Asp Trp Arg Phe Phe Asn Gly Ala Met Asn His Glu Ser Ser
        435                 440                 445
Gly Phe Thr Glu Glu Glu Arg Gln Leu Arg Lys Arg Ser Val Leu His
    450                 455                 460
Arg Leu Leu Arg Asn Trp Leu Val Phe Asn Tyr Gln Gln Gly Ser Pro
465                 470                 475                 480
Thr Trp Leu Ala His Gly Thr Leu Leu Ser Trp Tyr Trp Asn Ser Leu
                485                 490                 495
Met Phe Pro Trp Asp Tyr Asp Ile Asp Val Gln Met Pro Ile Lys Ser
            500                 505                 510
Leu Asn Asn Leu Cys Ala Asn Phe Asn Gln Ser Leu Ile Ile Glu Asp
        515                 520                 525
Leu Thr Glu Gly Tyr Ser Ser Phe Phe Leu Asp Cys Gly Ser Ser Ile
```

```
                530             535             540
Thr His Arg Thr Lys Gly Lys Gly Leu Asn Phe Ile Asp Ala Arg Phe
545                 550                 555                 560

Ile Asn Val Glu Thr Gly Leu Tyr Ile Asp Ile Thr Gly Leu Ser Thr
                565                 570                 575

Ser Gln Ser Ala Arg Pro Pro Arg Phe Ser Asn Ala Ser Lys Lys Asp
                580                 585                 590

Pro Ile Tyr Asn Cys Arg Asn Asn His Phe Tyr Ser His Asn Asn Ile
                595                 600                 605

Ala Pro Leu Lys Tyr Thr Leu Met Glu Gly Val Pro Ser Phe Ile Pro
                610                 615                 620

Gln Gln Tyr Glu Glu Ile Leu Arg Glu Tyr Thr Thr Gly Leu Thr
625                 630                 635                 640

Ser Lys His Tyr Asn Gly Asn Phe Phe Met Thr Gln Leu Asn Leu Trp
                645                 650                 655

Leu Glu Arg Asp Pro Met Leu Ala Leu Val Pro Ser Ser Lys Tyr Glu
                660                 665                 670

Ile Glu Gly Gly Gly Val Asp His Asn Lys Ile Ile Lys Ser Ile Leu
                675                 680                 685

Glu Leu Ser Asn Ile Lys Lys Leu Glu Leu Leu Asp Asp Asn Pro Asp
690                 695                 700

Ile Leu Glu Glu Val Ile Arg Thr Tyr Glu Leu Thr Ser Ile His His
705                 710                 715                 720

Lys Glu Met Gln Tyr Leu Ser Ser Val Lys Pro Asp Gly Asp Arg Ser
                725                 730                 735

Met Gln Ser Asn Asp Ile Thr Ser Ser Tyr Gln Glu Phe Leu Ala Ser
                740                 745                 750

Leu Lys Lys Phe Gln Pro Leu Arg Lys Asp Leu Phe Gln Phe Glu Arg
                755                 760                 765

Ile Asp Leu Ser Lys His Arg Lys Gln
                770                 775

<210> SEQ ID NO 19
<211> LENGTH: 1176
<212> TYPE: PRT
<213> ORGANISM: Saccharomyces cerevisiae
<220> FEATURE:
<223> OTHER INFORMATION: ScMnn4p

<400> SEQUENCE: 19

Met Leu Gln Arg Ile Ser Ser Lys Leu His Arg Arg Phe Leu Ser Gly
1               5                   10                  15

Leu Leu Arg Val Lys His Tyr Pro Leu Arg Arg Ile Leu Leu Pro Leu
                20                  25                  30

Ile Leu Leu Gln Ile Ile Ile Thr Phe Ile Trp Ser Asn Ser Pro
            35                  40                  45

Gln Arg Asn Gly Leu Gly Arg Asp Ala Asp Tyr Leu Leu Pro Asn Tyr
        50                  55                  60

Asn Glu Leu Asp Ser Asp Asp Ser Trp Tyr Ser Ile Leu Thr Ser
65                  70                  75                  80

Ser Phe Lys Asn Asp Arg Lys Ile Gln Phe Ala Lys Thr Leu Tyr Glu
                85                  90                  95

Asn Leu Lys Phe Gly Thr Asn Pro Lys Trp Val Asn Glu Tyr Thr Leu
                100                 105                 110

Gln Asn Asp Leu Leu Ser Val Lys Met Gly Pro Arg Lys Gly Ser Lys
            115                 120                 125
```

```
Leu Glu Ser Val Asp Glu Leu Lys Phe Tyr Asp Phe Asp Pro Arg Leu
        130                 135                 140

Thr Trp Ser Val Val Leu Asn His Leu Gln Asn Asn Asp Ala Asp Gln
145                 150                 155                 160

Pro Glu Lys Leu Pro Phe Ser Trp Tyr Asp Trp Thr Thr Phe His Glu
                165                 170                 175

Leu Asn Lys Leu Ile Ser Ile Asp Lys Thr Val Leu Pro Cys Asn Phe
                180                 185                 190

Leu Phe Gln Ser Ala Phe Asp Lys Glu Ser Leu Glu Ala Ile Glu Thr
            195                 200                 205

Glu Leu Gly Glu Pro Leu Phe Leu Tyr Glu Arg Pro Lys Tyr Ala Gln
        210                 215                 220

Lys Leu Trp Tyr Lys Ala Arg Asn Gln Asp Arg Ile Lys Asp Ser
225                 230                 235                 240

Lys Glu Leu Lys Lys His Cys Ser Lys Leu Phe Thr Pro Asp Gly His
                245                 250                 255

Gly Ser Pro Lys Gly Leu Arg Phe Asn Thr Gln Phe Gln Ile Lys Glu
                260                 265                 270

Leu Tyr Asp Lys Val Arg Pro Glu Val Tyr Gln Leu Gln Ala Arg Asn
            275                 280                 285

Tyr Ile Leu Thr Thr Gln Ser His Pro Leu Ser Ile Ser Ile Glu
        290                 295                 300

Ser Asp Asn Ser Thr Tyr Gln Val Pro Leu Gln Thr Glu Lys Ser Lys
305                 310                 315                 320

Asn Leu Val Gln Ser Gly Leu Leu Gln Glu Tyr Ile Asn Asp Asn Ile
                325                 330                 335

Asn Ser Thr Asn Lys Arg Lys Lys Asn Lys Gln Asp Val Glu Phe Asn
            340                 345                 350

His Asn Arg Leu Phe Gln Glu Phe Val Asn Asn Asp Gln Val Asn Ser
        355                 360                 365

Leu Tyr Lys Leu Glu Ile Glu Glu Thr Asp Lys Phe Thr Phe Asp Lys
        370                 375                 380

Asp Leu Val Tyr Leu Ser Pro Ser Asp Phe Lys Phe Asp Ala Ser Lys
385                 390                 395                 400

Lys Ile Glu Glu Leu Glu Glu Gln Lys Lys Leu Tyr Pro Asp Lys Phe
                405                 410                 415

Ser Ala His Asn Glu Asn Tyr Leu Asn Ser Leu Lys Asn Ser Val Lys
                420                 425                 430

Thr Ser Pro Ala Leu Gln Arg Lys Phe Phe Tyr Glu Ala Gly Ala Val
        435                 440                 445

Lys Gln Tyr Lys Gly Met Gly Phe His Arg Asp Lys Arg Phe Asn
        450                 455                 460

Val Asp Thr Leu Ile Asn Asp Lys Gln Glu Tyr Gln Ala Arg Leu Asn
465                 470                 475                 480

Ser Met Ile Arg Thr Phe Gln Lys Phe Thr Lys Ala Asn Gly Ile Ile
                485                 490                 495

Ser Trp Leu Ser His Gly Thr Leu Tyr Gly Tyr Leu Tyr Asn Gly Met
                500                 505                 510

Ala Phe Pro Trp Asp Asn Asp Phe Asp Leu Gln Met Pro Ile Lys His
            515                 520                 525

Leu Gln Leu Leu Ser Gln Tyr Phe Asn Gln Ser Leu Ile Leu Glu Asp
        530                 535                 540

Pro Arg Gln Gly Asn Gly Arg Tyr Phe Leu Asp Val Ser Asp Ser Leu
```

```
              545                 550                 555                 560

Thr Val Arg Ile Asn Gly Asn Gly Lys Asn Asn Ile Asp Ala Arg Phe
            565                 570                 575

Ile Asp Val Asp Thr Gly Leu Tyr Ile Asp Ile Thr Gly Leu Ala Ser
            580                 585                 590

Thr Ser Ala Pro Ser Arg Asp Tyr Leu Asn Ser Tyr Ile Glu Glu Arg
            595                 600                 605

Leu Gln Glu Glu His Leu Asp Ile Asn Asn Ile Pro Glu Ser Asn Gly
            610                 615                 620

Glu Thr Ala Thr Leu Pro Asp Lys Val Asp Asp Gly Leu Val Asn Met
625                 630                 635                 640

Ala Thr Leu Asn Ile Thr Glu Leu Arg Asp Tyr Ile Thr Ser Asp Glu
            645                 650                 655

Asn Lys Asn His Lys Arg Val Pro Thr Asp Thr Asp Leu Lys Asp Leu
            660                 665                 670

Leu Lys Lys Glu Leu Glu Glu Leu Pro Lys Ser Lys Thr Ile Glu Asn
            675                 680                 685

Lys Leu Asn Pro Lys Gln Arg Tyr Phe Leu Asn Glu Lys Leu Lys Leu
690                 695                 700

Tyr Asn Cys Arg Asn Asn His Phe Asn Ser Phe Glu Leu Ser Pro
705                 710                 715                 720

Leu Ile Asn Thr Val Phe His Gly Val Pro Ala Leu Ile Pro His Arg
            725                 730                 735

His Thr Tyr Cys Leu His Asn Glu Tyr His Val Pro Asp Arg Tyr Ala
            740                 745                 750

Phe Asp Ala Tyr Lys Asn Thr Ala Tyr Leu Pro Glu Phe Arg Phe Trp
            755                 760                 765

Phe Asp Tyr Asp Gly Leu Lys Lys Cys Ser Asn Ile Asn Ser Trp Tyr
            770                 775                 780

Pro Asn Ile Pro Ser Ile Asn Ser Trp Asn Pro Asn Leu Leu Lys Glu
785                 790                 795                 800

Ile Ser Ser Thr Lys Phe Glu Ser Lys Leu Phe Asp Ser Asn Lys Val
                    805                 810                 815

Ser Glu Tyr Ser Phe Lys Asn Leu Ser Met Asp Asp Val Arg Leu Ile
                    820                 825                 830

Tyr Lys Asn Ile Pro Lys Ala Gly Ile Glu Val Phe Thr Asn Leu Tyr
                    835                 840                 845

Asn Ser Phe Asn Val Thr Ala Tyr Arg Gln Lys Glu Leu Glu Ile Gln
850                 855                 860

Tyr Cys Gln Asn Leu Thr Phe Ile Glu Lys Lys Leu Leu His Gln
865                 870                 875                 880

Leu Arg Ile Asn Val Ala Pro Lys Leu Ser Ser Pro Ala Lys Asp Pro
            885                 890                 895

Phe Leu Phe Tyr Glu Lys Ala Met Trp Lys Asp Leu Ser Lys Ser Met
            900                 905                 910

Asn Gln Thr Thr Leu Asp Gln Val Thr Lys Ile Val His Glu Glu Tyr
            915                 920                 925

Val Gly Lys Ile Ile Asp Leu Ser Glu Ser Leu Lys Tyr Arg Asn Phe
            930                 935                 940

Ser Leu Phe Asn Ile Thr Phe Asp Glu Thr Gly Thr Thr Leu Asp Asp
945                 950                 955                 960

Asn Thr Glu Asp Tyr Thr Pro Ala Asn Thr Val Glu Val Asn Pro Val
                    965                 970                 975
```

```
Asp Phe Lys Ser Asn Leu Asn Phe Ser Ser Asn Ser Phe Leu Asp Leu
                980                 985                 990

Asn Ser Tyr Gly Leu Asp Leu Phe Ala Pro Thr Leu Ser Asp Val Asn
        995                 1000                1005

Arg Lys Gly Ile Gln Met Phe Asp Lys Asp Pro Ile Ile Val Tyr
    1010                1015                1020

Glu Asp Tyr Ala Tyr Ala Lys Leu Leu Glu Glu Arg Lys Arg Arg
    1025                1030                1035

Glu Lys Lys Lys Lys Glu Glu Glu Glu Lys Lys Lys Lys Glu Glu
    1040                1045                1050

Glu Glu Lys Lys Lys Lys Glu Glu Glu Lys Lys Lys Lys Glu
    1055                1060                1065

Glu Glu Glu Lys Lys Lys Lys Glu Glu Glu Glu Lys Lys Lys Lys
    1070                1075                1080

Glu Glu Glu Glu Lys Lys Lys Gln Glu Glu Glu Lys Lys Lys
    1085                1090                1095

Lys Glu Glu Glu Glu Lys Lys Lys Gln Glu Glu Gly Glu Lys Met
    1100                1105                1110

Lys Asn Glu Asp Glu Glu Asn Lys Lys Asn Glu Asp Glu Glu Lys
    1115                1120                1125

Lys Lys Asn Glu Glu Glu Glu Lys Lys Lys Gln Glu Glu Lys Asn
    1130                1135                1140

Lys Lys Asn Glu Asp Glu Glu Lys Lys Lys Gln Glu Glu Glu Glu
    1145                1150                1155

Lys Lys Lys Asn Glu Glu Glu Glu Lys Lys Lys Gln Glu Glu Gly
    1160                1165                1170

His Ser Asn
    1175

<210> SEQ ID NO 20
<211> LENGTH: 8
<212> TYPE: PRT
<213> ORGANISM: Saccharomyces cerevisiae
<220> FEATURE:
<223> OTHER INFORMATION: YIMpo1p

<400> SEQUENCE: 20

Lys Lys Lys Lys Glu Glu Glu Glu
1               5
```

YLMPO1 GENE DERIVED FROM YARROWIA LIPOLYTICA AND A PROCESS FOR PREPARING A GLYCOPROTEIN NOT BEING MANNOSYLPHOSPHORYLATED BY USING A MUTATED YARROWIA LIPOLYTICA IN WHICH YLMPO1 GENE IS DISRUPTED

CROSS REFERENCE TO RELATED APPLICATIONS

This application is the National Stage of International Application No. PCT/KR2007/006164, filed Nov. 30, 2007, which claims priority to Korean Application No. 10-2007-0043806, filed May 4, 2007, and Korean Application No. 10-2007-0057635, filed Jun. 13, 2007.

REFERENCE TO A SUBSTITUTE SEQUENCE LISTING SUBMITTED ELECTRONICALLY VIA EFS-WEB

The content of the electronically submitted sequence listing, file name: sequencelisting_v3_ascii.txt; size: 61,393 bytes; and date of creation: May 2, 2011, filed herewith, is incorporated herein by reference in its entirety.

TECHNICAL FIELD

The present invention relates to an YlMPO1 gene (Mannosyl Phosphorylation of Oligosaccharide) of *Yarrowia lipolytica*, which plays an essential role in mannosylphosphorylation of N-linked oligosaccharide, a *Yarrowia lipolytica* mutant strain deficient in the MPO1 gene, and a method for producing a recombinant glycoprotein using the mutant strain.

BACKGROUND ART

Most therapeutic proteins are glycoproteins where oligosaccharides are covalently bonded to amino acid residues as they pass through the secretory pathway. The sugar moieties are known to greatly affect biological activity and function of the glycoproteins. To date, to solve the problems such as immune response in the body, therapeutic glycoproteins are commonly produced using animal cell expression systems. However, there are drawbacks to animal cell culture systems, which include low yield, high cost, and potential viral and prion contamination. In this regard, many attempts have been made to use, as an alternative to animal cell expression systems, yeast expression systems, which are efficient and high-yield expression systems, and share the early steps of the N-linked glycosylation pathway of higher animal cells.

Microbial eukaryotes, yeasts have advantages of rapidly producing a high concentration of proteins, being easily genetically engineered, and having no risk of infections by human or animal virus and prion to ensure safety. However, the final oligosaccharides synthesized in yeasts have different type of sugar moieties from those of human, and thus may cause immune responses in animal cells. To solve the above problems, there is a need for glycotechnology, by which the yeast glycosylation pathway is remodeled to express glycoproteins having oligosaccharides similar to those of human glycoproteins.

A traditional yeast, *Saccharomyces cerevisiae* has a hypermannosylated N-linked oligosaccharide composed of a series of 50 to 200 mannose residues attached to a core oligosaccharide chain and decorated with the terminal alpha 1,3-linked mannoses (Dean, Biochim. Biophys. Acta., 1426, p.309-322, 1999). In addition, mannosylphosphate is added to the core and outer chain of oligosaccharide (Ballow, 1990, Methods Enzymol. 185: 440-470), and a glycoprotein with mannosylphosphorylated oligosaccharide was reported to induce immune responses when injected to animals (Rosenfeld and Ballou, 1974, J. Biol. Chem. 249: 2319-2321). Thus, there is an attempt to humanize glycosylation pathway by disrupting OCH1 and MNN4 genes, which mediates outer chain initiation and participates in addition of mannosylphosphate, respectively (Jigami and Odani, Biochim, Biophys. Acta 1426, 335-345, 1999). However, mannosylphosphorylation was not completely regulated in MNN4-disrupted strains, even though the extent was less than that in a wild-type strain (Odani et al., Glycobiology, 6, p.805-810, 1996).

There is an attempt to humanize the glycosylation pathway by eliminating mannosylphosphorylation in a methylotrophic yeast, *Pichia pastoris*, as well as in the traditional yeast. A PNO1 (Phosphorylmannosylation of N-linked Oligosacharides) gene, which plays an important role in mannosylphosphorylation in *Pichia pastoris*, was cloned by using a sequence of MNN4 gene of *Saccharomyces cerevisiae* as a probe (Miura et al., Japan), and there is a report that the mannosylphosphorylation can be controlled by the elimination of PNO1 gene (WO 01/88143; Miura et al., 2004, Gene 324; 129-137).

However, it was found by GlycoFi Inc. that the disruption of the PNO1 may suppress the mannosylphosphorylation, but does not completely eliminate it, leading to application of the invention (US2006/0160179). In the invention, a BLAST search was performed for the amino acid sequence of Mnn4 protein (SEQ ID NO: 19) from *Saccharomyces cerevisiae* against the genome of *Pichia pastoris* (Integrated Genomics, Chicago, Ill.). This search resulted in the identification of three genes, which were designated as MNN4A, MNN4B and MNN4C, respectively. They also found that the mannosylphosphorylation can be completely eliminated by double disruption of MNN4A and PNO1 genes.

A dimorphic, non-pathogenic yeast, *Yarrowia lipolytica* has been used on a large scale for the production of citric acid and of single-cell proteins, and is characterized by excessive secretion of extracellular proteins such as protease and lipase. Also, *Yarrowia lipolytica* has been considered as an excellent host system for producing therapeutic glycoproteins, since it exhibits higher protein secretion efficiency than the traditional yeast *Saccharomyces*, has co-translational protein modification similar in animal cells (Boisrame et al., J. Biol. Chem., 273, p.30903-30908, 1998), has a lower number of mannose attached to the core chain than *Saccharomyces cerevisiae* (Madzak et al., J. Biotechnol., 10, p.63-81, 2004), and has no immunogenic alpha 1,3-linked mannose. To express and secrete therapeutic glycoproteins derived from human in *Yarrowia lipolytica*, the glycosylation pathway of *Yarrowia lipolytica* has to be understood, but is still poorly understood (Jaagar et al., Yeast, 20, p.633-644, 2003, Barnay-Verdier et al., Microbiology, 150, p.2185-2195, 2004).

To develop *Yarrowia lipolytica* as a host for secretory expression of therapeutic glycoproteins, the present inventors have conducted studies on the glycosylation pathway of *Yarrowia lipolytica*, and manufactured a strain comprising a disrupted YlOCH1 gene which mediates outer chain initiation. However, upon disruption of the YlOCH1 gene, the mannosylphosphorylation was found to be more activated.

DISCLOSURE OF INVENTION

Technical Problem

Accordingly, the present inventors performed a BLAST search for the amino acid sequence of Mnn4 protein from Saccharomyces cerevisiae, which plays an essential role in mannosylphosphorylation, against the genome of Yarrowia lipolytica (cbi.labri.fr/Genolevures/elt/YALI), resulting in identification of a novel YlMPO1 gene (SEQ ID NO: 1) of Yarrowia lipolytica. They also manufactured a YlMPO1 disrupted strain (Ylmpo1Δ), and performed analysis on secretory proteins and main ingredients of cell wall. Consequently, they found that synthesis of oligosaccharide free of mannosylphosphate can be realized by the disruption of YlMPO1 gene (SEQ ID NO: 1) in Yarrowia lipolytica, thereby completing the present invention.

Technical Solution

It is an object of the present invention to provide a novel YlMPO1 gene, which plays an essential role in mannosylphosphorylation in the glycosylation pathway of Yarrowia lipolytica.

It is another object of the present invention to provide a Yarrowia lipolytica mutant strain capable of producing, glycoproteins free of mannosylphosphate by disruption of the YlMPO1 gene (SEQ ID NO: 1).

It is still another object of the present invention to provide a method for producing a recombinant glycoprotein, in which a nucleic acid molecule encoding a foreign protein is introduced into the Yarrowia lipolytica mutant strain disrupted in the YlMPO1 gene to produce glycoproteins free of yeast-specific mannosylphosphate, thereby being used as a therapeutic glycoprotein.

Advantageous Effects

To manufacture a yeast expression system for producing therapeutic glycoproteins derived from human by humanization of glycosylation pathway of Yarrowia lipolytica, it is essential to control the addition of yeast-specific mannosylphosphate. As described above, the results of HPLC profile analysis and alcian blue staining showed that the addition of mannosylphosphate to the core and outer sugar chains was completely suppressed in the YlMPO1 disrupted strain (Ylmpo1Δ) developed according to the present invention. In Saccharomyces cerevisiae or Pichia pastoris, it was not observed that the mannosylphosphorylation is completely suppressed by only the single gene deletion.

Accordingly, the method for suppressing mannosylphosphorylation by disruption of the YlMPO1 gene according to the present invention can be usefully applied to development of strains producing human-type glycoproteins, with the aid of other techniques for redesigning glycosylation pathways.

BRIEF DESCRIPTION OF DRAWINGS

FIG. 1 shows a nucleotide sequence of 2,135 by corresponding to an YlMFO1 gene (SEQ ID NO: 1) and a deduced amino acid sequence of YlMpo1 protein (SEQ ID NO 2);

FIGS. 2 to 4 show a multiple alignment of amino acid sequences of Mnn4 protein, which plays an important role in mannosylphosphorylation of yeast and fungi, the corresponding proteins, and YlMpo1 protein (SEQ ID NO: 2) of Yarrowia lipolytica by homology comparison program (www.ncbi.nlm.nih.gov/BLAST/), in which the information for the species name, GeneBank Accession Number, or PCT patent number of each protein is as follows: AfMnn4p (Aspergillus fumigatus, XP_752633) (SEQ ID NO: 12); CaMnm4p (Candida albicans, AAL86704) (SEQ ID NO: 13); NcLac1p (Neurospora crassa, CAB91733); PpMnn4Ap (Pichia pastoris, WO2005/060519) (SEQ ID NO: 14); PpMnn4Bp (Pichia pastoris, WO2005/060519) (SEQ ID NO: 15); PpMnn4Cp (Pichia pastoris, WO2005/060519) (SEQ ID NO: 16); PpPno1p (Pichia pastoris, BAD06252) (SEQ ID NO: 18); ScMnn4p (Saccharomyces cerevisiae, NP_012721) (SEQ ID NO 19); YlMpo1p (Yarrowia lipolytica) (SEQ ID NO: 2);

FIG. 5 is the results of analysis of identity and similarity (FIG. 5a) between the YlMpo1 protein (SEQ ID NO: 2) of Yarrowia lipolytica and other proteins, which are presumed to play an important role in mannosylphosphorylation of yeast and fungi, and a tree diagram (FIG. 5b) showing relationships between the proteins (performed by using the online program (align.genome.jp/);

FIG. 6 is a schematic diagram showing DNA recombination for disruption of the YlMPO1 gene of Yarrowia lipolytica (SEQ ID NO: 1) (FIG. 6a) and the result of Southern blotting for the YlPO1 disrupted strain (FIG. 6b), in which each lane represents the following strains; Lane 1: wild-type strain (YlMPO1), Lane 2: Ylmpo1 disrupted strain popped out of selectable marker YlURA3 (Ylmpo1::tc-YlURA3-tc), Lane 3: Ylmpo1 disrupted strain (Ylmpo1:tc);

FIG. 7 is a schematic diagram showing the construction of recombinant expression vector which expresses endoglucanase I (EGI) derived from Trichoderma reesei; and FIG. 8 is the result of analyzing the characteristics related to glycosylation of Ylmpo1 disrupted strains. FIG. 8a is the result of HPLC analysis on N-linked oligosaccharides of glycoproteins (Endoglucanase I, EGI) secreted from Ylmpo1 disrupted strains, manufactured by using the wild-type strain and YlOCH1 disrupted strain as a mother strain (a) wild-type strain, (b) Ylmpo1 disrupted strain, (c) Yloch1 disrupted strain, (d) Ylmpo1/Yloch1 double disrupted strain). FIG. 8b is the result of HPLC analysis on N-linked oligosaccharides of mannoproteins derived from the wild-type strain and YlMPO1 disrupted strain, in which EGI and mannoproteins isolated and purified from each media and cell wall were treated with a peptide N-glycosidase F (PNGase F) to cleave the sugar chains, and the sugar chains were labeled with a fluorescent compound at their reducing end. A retention time of standard sugar chain is marked with an arrow (M7, $Man_7GlcNAc_2$-PA; M8, $Man_8GlcNAc_2$-PA; M9, $Man_9GlcNAc_2$-PA; M10, $Man_{10}GlcNAc_2$-PA), and peaks corresponding to sugar chains with mannosylphosphate are marked with *: *[1] corresponds to an M8 type sugar chain with monomannosylphosphate, and *[2] corresponds to an M9 type sugar chain with monomannoyslphosphate. FIG. 8c is the result of alcian blue staining of Ylmpo1 disrupted strain (Ylmpo1::tc) and wild-type strain, in which the strains grown to stationary phase were reacted with 0.1% alcian blue at room temperature for 30 min, and then the staining level was scanned to compare the color difference between two strains. Since the extent of alcian blue staining is correlated with the amount of mannosylphosphate attached to sugar chain of mannoprotein in cell wall, it can be seen that the amount of mannosylphosphate is remarkably reduced in the Ylmpo1 disrupted strain.

BEST MODE FOR CARRYING OUT THE INVENTION

The present invention relates to a novel YlMPO1 gene (SEQ ID NO: 1) which plays an essential role in mannosylphosphorylation of an industrial yeast, Yarrowia lipolytica, and to a method for preparing a host system capable of producing a recombinant glycoprotein free of mannosylphosphate by disruption of the gene.

As used herein, the term "glycoprotein", refers to a protein that is glycosylated on one or more asparagines, or one or more serine or threonine residues, or is glycosylated on asparagine and serine or threonine residues. As used herein, the term "mannosylphosphate" refers to a non-human sugar residue found in yeast and fungi, and is transferred to both the core and outer sugar chains of glycoproteins (Jigami Y & Odani T, Biochimica et Biophysica Acta 1426, p.335-345, 1999).

The present inventors performed a BLAST search for the amino acid sequence of Mnn4 protein (SEQ ID NO: 19) from *Saccharomyces cerevisiae,* which plays an essential role in mannosylphosphorylation, against the genome of *Yarrowia lipolytica* (cbi.labri.fr/Genolvures/elt/YALI), resulting in identification of a novel YlMPO1 gene (SEQ ID NO: 1) of *Yarrowia lipolytica.* A base sequence of the gene is described in SEQ ID NO. 1, and an amino acid sequence of deduced Ylmpo1 protein is described in SEQ ID NO. 2.

In one aspect, the present invention provides an Ylmpo1 protein having the amino acid sequence represented by SEQ ID NO. 2, which plays an important role in mannosylphosphorylation.

In another aspect, the present invention provides a nucleic acid molecule encoding the Ylmpo1 protein (SEQ ID NO:2), and a nucleic acid molecule which has 75% or higher, preferably 85%, and more preferably 90% or higher homology therewith arid encodes a polypeptide which exhibits an activity of the Ylmpo1 protein (SEQ ID NO: 2). Preferably, the nucleic acid molecule is a nucleic acid molecule having a base sequence of SEQ ID NO. 1, and includes an analogue thereof or a fragment thereof.

The term "homology", as used for the YlMPO1 gene (SEQ ID NO: 1) derived from *Yarrowia lipolytica,* is intended to indicate the degree of similarity to the base sequence of a wild type, and includes a base sequence having an identity of preferably 75% or higher, more preferably 85% or higher, even more preferably 90% or higher, and most preferably 95% or higher, with the base sequence of the YlMPO1 gene (SEQ ID NO:1) of the present invention. It will be appreciated by those skilled in the art that a nucleic acid molecule which has the homology in the above range and encodes a polypeptide having the same activity can be readily prepared using a method known in the art such as recombinant DNA technology, resulting from substitution, addition or deletion of one or more base sequences of the YlMPO1 gene (SEQ ID NO:1) according to the present invention. This homology comparison may be performed by using a commercially available comparison program. A commercially available computer program may express homology between two or more sequences in a percentage, and a homology (%) may be calculated for adjacent sequences.

A novel gene and its resulting protein may be analyzed by sequence comparison with homologous protein families present in various organisms to predict its function. The sequence comparison may he performed by using a commercially available analysis software or a web based analysis system. In the present invention, a protein resulting from the novel gene of *Yarrowia lipolytica* was analyzed using a web based analysis system to compare identity and similarity with homologous protein families.

The term "identity", as used for the YlMPO1 protein (SEQ ID NO: 2) derived from *Yarrowia lipolytica,* means that a position in the compared sequence is occupied by the same amino acid residue, upon sequence comparison of proteins derived from various organisms, and expresses the percentage (%) of same amino acid residues being present at a given position. In addition, the term "similarity" means that a position in the compared sequence is occupied by the amino acid residue with a similar chemical property, upon sequence comparison of proteins, and expresses the percentage (%) of amino acid residue with a similar chemical property being present at a given position.

To prepare a more preferred host capable of producing human-type glycoproteins by regulating the mannosylphosphorylation of *Yarrowia lipolytica,* the present inventors performed polymerase chain reaction to obtain the YlMPO1 gene (SEQ ID NO: 1) which plays an essential role in mannosylphosphorylation, and then constructed an YlMPO1 disruption vector by using the PCR product. Then, they transformed *Yarrowia lipolytica* with the YlMPO1 disruption vector to manufacture a YlOCH1 disrupted strain (*Yarrowia lipolytica* mpo1Δ) (Example 3), which was deposited at KCTC (Korean Collection for Type Cultures; Korea Institute of Bioscience and Biotechnology, 52, Ueun-dong, Yusung-gu, Daejeon, Korea) on Mar. 27, 2007 under accession number KCTC 11102BP.

In still another aspect, the present invention relates to a mutant strain producing glycoproteins free of mannosylphosphate, prepared by disruption of the YlMPO1 gene (SEQ ID NO: 1) which plays an essential role in mannosylphosphorylation, and the mutant strain is preferably a *Yarrowia lipolytica* mutant strain Ylmpo1Δ, deposited under accession number KCTC 11102BP.

The specific disruption, that is, inactivation of a target gene on the genome may be easily achieved by those skilled in the art using a method established in the art, and the method is not particularly limited. The present inventors first constructed an YlMPO1 disruption vector using the YlMPO1 gene (SEQ ID NO: 1), and transformed *Yarrowia lipolytica* with the vector to induce a homologous recombination between the genome and the vector. Selection markers useful for the construction of the YlMPO1 disruption vector are not particularly limited, but include markers providing selectable phenotypes, such as drug resistance, auxotrophy, resistance to cytotoxic agents, or surface protein expression. In the practice of the present invention, YlURA3 was used as a selection marker.

An HPLC analysis and alcian blue staining were performed to analyze sugar chains attached to glycoproteins which were expressed in the prepared YlMPO1 deleted stain (Ylmpo1Δ) (see FIG. 8). From the result of oligosaccharide profile analysis on secretory proteins and cell wall proteins expressed in the Ylmpo1Δ strain, neutral sugars were found to show the same pattern as those of a wild-type, and acidic sugars produced by mannosylphosphorylation were not observed. In addition, it was found that the Ylmpo1Δ strain was hardly stained with alcian blue, as compared to the wild-type strain, indicating that the addition of mannosylphosphate to the sugar chain of cell wall proteins which were expressed in the Ylmpo1Δ strain was suppressed.

The above results indicate that binding of mannosylphosphate to both the core and outer sugar chains can be suppressed by deletion of only the YlMPO1 gene (SEQ ID NO: 1) of *Yarrowia lipolytica.* Upon the deletion of ScMNN4 gene (SEQ ID NO 19), a traditional yeast, *Saccharomyces cerevisiae* showed a remarkable decrease in alcian blue staining. However, from the result of structural analysis on its sugar chains, it was found that the addition of mannosylphosphate to the core sugar chain was not completely suppressed. In *Pichia pastoris,* four homologous genes including PpPNO1, PpMNN4A, PpMNN4B and exist, and the mannosylphosphorylation was completely suppressed by a double deletion of PpPNO1 and PpMNN4B. In particular, the disruption of only the PpPNO1 gene did not cause a reduction in alcian blue staining. Thus, the PpPNO1 gene is considered not to play an essential role in addition of mannosylphosphate to outer sugar chains.

As described above, since the mannosylphosphorylation can be suppressed by disruption of only one gene, *Yarrowia lipolytica* has a better advantage, as compared to *Saccharomyces cerevisiae* or *Pichia pastoris*. Such advantage is more beneficial for humanization of glycosylation pathway in yeast, which requires deletion of yeast-specific genes and introduction of various new genes.

On the other hand, in *Yarrowia lipolytica*, the yeast-specific glycosylation can be completely eliminated by a double disruption of YlOCH1 and YlMPO1 genes (SEQ ID NO: 1), which mediates outer chain initiation and participates in mannosylphosphorylation, respectively.

In still another aspect, the present invention provides a method for preparing a mutant strain capable of producing various human-compatible oligosaccharides, in which the YlMPO1 disrupted strain (Ylmpo1Δ) is additionally redesigned to have a double disruption of YlMPO1 and YlOCH1 gene as a preferable example. In the present invention, a *Yarrowia lipolytica* mutant strain (och1Δmpo1Δ) was manufactured by a double disruption of YlMPO1 (SEQ ID NO: 1) and YlOCH1 genes (Example 4), which was deposited at KCTC (Korean Collection for Type Cultures; Korea Institute of Bioscience and Biotechnology, 52, Ueun-dong, Yusung-gu, Daejeon, Korea) on Apr. 26, 2007 under accession number KCTC 11126BP.

In still another embodiment, the present invention relates to a method for producing various human-type glycoproteins using the *Yarrowia lipolytica* mutant strain, and to human-type glycoproteins produced according to the same method.

Since glycoproteins prepared according to the present invention, which are expressed in the *Yarrowia lipolytica* mutant strain deficient in YlMPO1 gene (SEQ ID NO: 1) or both YlMPO1 and YlCHO1 genes, have humanized sugar chains to be less immunogenic in humans, and are identical or similar to proteins produced in humans with respect to solubility, sensitivity to proteases, trafficking, transport, secretion, recognition by other proteins or factors, or the like, they may be suitable for therapeutic use.

A produced glycoprotein may be purified by an ordinary method, and the purification protocol may be determined according to the properties of the specific protein to be purified. This determination is considered as an ordinary skill to those skilled in the art. For example, a target protein may be purified by a typical isolation technique, such as precipitation, immunoadsorption, fractionation, and various chromatographic methods.

Glycoproteins capable of being produced according to the present invention are exemplified by cytokines (e.g., EPO, interferon-alpha, interferon-beta, interferon-gamma, G-CSF, etc.), clotting factors (e.g., VIII factor, IX factor, human protein C), antibodies for therapeutic use (e.g., immunogloblulins, Fab, double specific antibodies, monovalent antibodies, diabody, etc.) and Fc fusion proteins, therapeutic enzymes (e.g., glucocerebrosidase, alpha-galactosidase, alpha-L-iduronidase, alpha-glucosidase, etc.), endothelial growth factor, growth hormone releasing factor, Typanosoma cruzi transsialidase, HIV envelope protein, influenza virus A haemagglutinin, influenza neuraminidase, bovine enterokinase activator, bovine herpes virus type-1 glycoprotein D, human angiostatin, human B7-1, B7-2 and B-7 receptor CTLA-4, human tissue factor, growth factors (e.g., platelet-derived growth factor), human alpha-antitrypsin, tissue plasminogen activator, plasminogen activator inhibitor-1, urokinase, plasminogen, and thrombin, but are not limited thereto.

MODE FOR THE INVENTION

Hereinafter, a better understanding of the present invention may be obtained through the following examples which are set forth to illustrate, but are not to be construed as the limit of the present invention.

EXAMPLE 1

Identification of YlMPO1 gene

A BLAST search was performed using an amino acid sequence of Mnn4 protein (SEQ ID NO: 19) from *Saccharomyces cerevisiae*, which plays a crucial role in mannosylphosphorylation, against the genome of *Yarrowia lipolytica* to identify the YlMPO1 gene (SEQ ID NO: 1) of *Yarrowia lipolytica* of the present invention, and the homologous gene encodes a protein consisting of 644 amino acids (FIG. 1).

The present inventors also found the MNN4 gene and corresponding gene families in eukaryotes including *Aspergillus fumigatus, Candida albicans, Neurospora crassa, Pichia pastoris, Saccharomyces cerevisiae,* and *Yarrowia lipolytica*, and they compared amino acid sequences encoding them with each other (FIGS. 2 to 4). The YlMpo1 protein (SEQ ID NO: 2) does not contain a repeating sequence (Lys-Lys-Lys-Lys-Glu-Glu-Glu-Glu) (SEQ ID NO: 20) consisting of four lysines (Lys) and four glutamic acids (Glu), found in the Mnn4 protein (SEQ ID NO: 19) of *Saccharomyces cerevisiae*.

FIG. 5 is the results of analysis of identity and similarity (FIG. 5a) and a tree diagram (FIG. 5b) which show relationships between the proteins from each species. The Mpo1 protein (SEQ ID NO: 2) of *Yarrowia lipolytica* exhibited a 40% identity with that of *Saccharomyces cerevisiae*, a 34% identity with that of *Candida albicans*, a 33% identity with the Pno1 protein (SEQ ID NO: 18) of *Pichia pastoris*, a 32% identity with the Mnn4A protein (SEQ ID NO: 14) of *Pichia pastoris*, a 27% identity with the Mnn4B protein (SEQ ID NO: 15) of *Pichia pastoris*, a 33% identity with the Mnn4C protein (SEQ ID NO: 16) of *Pichia pastoris*, a 41% identity with that of *Neurospora crassa* (SEQ ID NO: 17), and a 37% identity with that of *Aspergillus fumigatus* (SEQ ID NO: 12). As shown in the tree diagram of FIG. 5b, the YlMpo1 protein (SEQ ID NO: 2) was found on the different branch from the Mnn4 protein (SEQ ID NO: 19) of *Saccharomyces cerevisiae* or the Pno1 protein (SEQ ID NO: 18) of *Pichia pastoris*, and taxonomically similar to the Mnn4 proteins derived from fungus such as *Neurospora crassa* (SEQ ID NO: 17) and *Aspergillus fumigatus* (SEQ ID NO: 12). Thus, it can be thought that the YlMpo1 (SEQ ID NO: 2) protein belongs to a protein group, which is responsible for mannosylphosphorylation in yeast and fungus, but exhibits different properties from the Mnn4 protein (SEQ ID NO: 19) of *Saccharomyces cerevisiac*, or the Pno1 (SEQ ID NO: 18) and Mnn4A (SEQ ID NO: 14), Mnn4B (SEQ ID NO: 15), Mnn4C (SEQ ID NO: 16) proteins of *Pichia pastoris*, of which properties are known.

EXAMPLE 2

Construction of YlMPO1 Disruption Vector

To disrupt the YlMPO1 gene (SEQ ID NO: 1) in *Yarrowia lipolytica*, a disruption vector was constructed using an YlURA3 selectable marker cassette of FIG. 6a, as follows. A genomic DNA of *Yarrowia lipolytica* SMS397A (MATA ade1 ura3 xpr2) strain was subjected to polymerase chain reaction (PCR) using a Pfu polymerase (Neurotics, Korea)

and two pairs of primer sets, YlMPO1-F1 (CAACACAC-CATCGGAGAC) (SEQ ID NO. 3) and YlMPO1-R1 (CCATGGATCCGTAGATCTCTGC-CGAAAATCAGACAG) (SEQ ID NO. 4), and YlMPO1-F2 ( AGATCTACGGATCCATGGATCCAGGAGAGACCAGAG) (SEQ ID NO: 5) and YlMPO1-R2 (GTTGCGTCAT-TCTCTCCA) (SEQ ID NO. 6) to obtain two fragments of 571 hp and 477 bp, respectively. Then, fusion polymerase chain reaction (fusion PCR) was performed using two fragments as a template, a primer set of YlMPO1-F1 (SEQ ID NO: 3) and YlMPO1-R2 (SEQ ID NO: 6), and an Ex Tag polymerase (Takara, Japan) to obtain a fused fragment (1,066 bp) fused by a linker sequence (18 bp; AGATCTACGGATCCATGG) (SEQ ID NO. 7). The fused fragment was subcloned into a pGEM T easy vector (Promega, USA) to construct a pT-YlMPO1+ vector (4,084 bp). A tc-YlURA3-tc selectable marker was cleaved from a pYLUB vector (Song et al., J. Microbiology, 41, p121-128, 2003) using restriction enzymes. BamHI and BglII, and the product (2,783 bp) was cloned into a BglII site of the pT-YlMPO1+ vector to construct an Ylmpo1::tc-YlURA3-tc disruption vector, a pT-YlMPO1D vector (6,867 bp).

EXAMPLE 3

Establishment of Ylmpo1 Disrupted *Yarrowia lipolytica* Strain

The YlMPO1 gene (SEQ ID NO: 1) of *Yarrowia lipolytica* was disrupted using the gene disruption vector constructed in Example 2. An YlMPO1 disrupted strain (M4D3) and a M4D3P1 strain, in which the YlURA3 selectable marker was removed therefrom, were manufactured as follows. First, to disrupt the YlMPO1 gene (SEQ ID NO: 1), the Ylmpo1::tc-YlURA3-tc disruption vector, the pT-YlMPO1 D vector were cleaved with a restriction enzyme, NotI and a wild type SMS397A was transformed with the resulting fragment (3,849 bp). Transformants were selected on SC-URA selection media (2% glucose, 0.67% yeast nitrogen base w/o amino acid, DO supplement-URA). Then, the selected transformants were subjected to polymerase chain reaction to select YlMPO1 disrupted strains, designated as M4D3 (Ylmpo1::tc-NURA3-tc). The selected M4D3 strain was cultured in media supplemented with 5-fluorootic acid (5-FOA, 0.675 g/liter), and the YlURA3 selectable marker cassette was popped out of the M4D3 strain. The resulting strain was designated as M4D3P1 (Ylmpo1Δ, Ylmpo1::tc). All of the strains were subjected to Southern blotting, and the results are shown in FIG. 4B (lane 1: SMS397A, lane 2: M4D3P1, lane 3: M4D3).

EXAMPLE 4

Establishment of Yloch1/Ylmpo1 of double disrupted *Yarrowia lipolytica* Strain

To establish an YlOCH1 disrupted *Yarrowia lipolytica*, an YlOCH1 disruption vector was constructed using an YlURA3 selectable marker cassette in the same manner as in Example 2. The genomic DNA of *Yarrowia lipolytica* SMS397A strain was subjected to polymerase chain reaction using two pairs of primer sets, YlOCH1-F1 (ACTTTTTGCATCTGCGGAC) (SEQ ID NO: 8) and YlOCH1-R1 ( CCATGGATCCGTAGATCTAGGAGTTCGAAGACGTTG) (SEQ ID NO 9), and YlOCH1-F2 ( AGATCTACGGATCCATGGGACCGACTCTGTCTTCGA) (SEQ ID NO 10) and YlOCH1-R2 (CATCCTCCT-GATATACGC) (SEQ ID NO: 11) to obtain fragments containing a portion of N- and C-terminus of YlOCH1 gene. Then, fusion polymerase chain reaction was performed using two fragments as a template and a primer set of YlOCH1-F1 (SEQ ID NO:8) and YlOCH1-R2 (SEQ ID NO:10) to obtain a fused fragment fused by a linker sequence of SEQ ID NO. 7 used in Example 2. The fused fragment was subcloned into a pGEM T easy vector to construct a pT-YlOCH1+ vector. A tc-YlURA3-tc selectable marker was cleaved from a pYLUB vector, and the fragment was cloned into the pT-YlOCH1+ vector to construct an Yloch1::tc-YlURA3-tc disruption vector, a pT-YlOCH1D vector. To disrupt the YlOCH1 gene, the pT-YlOCH1D vector was cleaved with a restriction enzyme, NotI and a wild type *Yarrowia lipolytica* was transformed with the resulting fragment. Transformants were selected on SC-URA selection media. Then, the selected transformants were subjected to polymerase chain reaction to select YlOCH1 disrupted strains. The selected strain was cultured in media supplemented with 5-fluorootic acid, and the YlURA3 selectable marker cassette was popped out of the strain to give a strain (Yloch1Δ, Yloch1::tc). In addition, the strain (Yloch1Δ) was subjected to genetic recombination as performed in Example 3 using the pT-YlMPO1D vector prepared in Example 2 to manufacture a Yloch1Δ/Ylmpo1Δ double disrupted *Yarrowia lipolytica* strain (Yloch1::tc Ylmpo1::tc).

EXAMPLE 5

Construction of Model Glycoprotein-expressing Host

To analyze glycoproteins expressed in a wild-type *Yarrowia liolytica* and strains disrupted in glycosylation-related genes, strains expressing endoglucanase I (EGI), derived from *Trichoderma reesei*, were manufactured as follows. An EGI expressing vector, pXCSIn(His) (Park et al. Appl Biochem Biotechnol, 87, 1-15, 2000) was treated with EcoRI and ClaI, so as to isolate an EcoRI/ClaI fragment of about 3.5 kb containing a promoter of XPR2 gene encoding AEP (alkaline extracellular protease) derived from *Yarrowia*, an endoglucanase (EGI) gene tagged with 6 histidine residues at the C-terminus, and a terminator sequence of XPR2 gene. The fragment was introduced into a pAUX-1 vector (pIMR53, Sohn et al., J. Bacteriol, 180, 6736-42, 1998) treated with EcoRI and ClaI to construct a pAUXEGI vector (FIG. 7).

Then, a one-step transformation method (Chen et al., Appl. Microbiol Biotechnol. 48, p.232-235, 1997) was performed to introduce the vector into *Yarrowia lipolytica*. That is, a wild-type strain and an Ylmpo1Δ strain were smeared on YPD solid media, respectively and cultured for 16 to 24 hrs. Then, a loop of $5\times10^7$ cell was suspended in 100 μl of one-step buffer [50% (w/v) PEG 4000; 2M DTT; 2M lithium acetate (pH6.0); single-strand carrier DNA (10 μg/μl)], and 500 ng or more of the recombinant vector pAUXEGI were added thereto, followed by mixing well. The transformed cells were incubated in a water bath at 39° C. for 1 hr, spread on selective minimal media, and then cultured at 28° C. for 3 to 4 days to obtain transformants.

EXAMPLE 6

Structural Analysis of N-linked Oligosaccharide of Ylmpo1 Disrupted Strains

To analyze the structure of oligosaccharides Which were attached to secretory glycoproteins expressed in a wild-type *Yarrowia lipolytica*, and Ylmpo1Δ, Yloch1Δ and Yloch1Δ/Ylmpo1Δ mutant strains, the following method was employed. First, the strains precultured in YPD (1% yeast extract, 2% peptone, 2% glucose) media were inoculated in YPDm (1% yeast extract, 1% proteose peptone 0.1% glucose, 50 mM sodium phosphate buffer solution (p1-16.8)), and cultured at 28° C. for 30 hrs. The secreted EGI proteins in culture media were recovered using a cellulose membrane (YM-30, Millipore), and passed through a nickel column to selectively isolate EGI proteins tagged with 6 histidine residues at the C-terminus. The isolated EGI proteins were treated with a peptide-N-glycosidase F (PNGase-F) to cleave the N-linked oligosaccharides on the EGI proteins. Then, the oligosaccharides were isolated and purified using PGC (porous graphite column), and then labeled with a fluorescent compound, 2-aminopyridine (PA) at their reducing end. An HPLC analysis was performed to compare the profile of the N-linked oligosaccharide between two strains. The HPLC analysis (Waters, USA) was performed using an amine column (Asahipak NH2P-504E, Showa denko, Japan), and a linear gradient of a solvent A (0.2 M triethylamine-acetic acid:acetonitrile=1:9, pH 7.3) and a solvent B (0.2 M triethylamine-acetic acid:acetonitrile=9:1, pH 7.3) at a ratio of 80:20 to 5:95 and a flow rate of 1 ml/min for 52 min. The oligosaccharides labeled with a fluorescent compound (PA) were detected by fluorescence (excitation wavelength=320 nm and emission wavelength=400 nm) using a fluorescence detector connected to HPLC.

In addition, in order to analyze cell wall mannoproteins derived from the wild-type *Yarrowia lipolytica* and Ylmpo1Δ strain, the strains were grown to stationary phase, and then their oligosaccharides from cell wall mannoproteins were analyzed as follows. The strains precultured in YPD media were inoculated in 200 ml of YPD media, and grown to stationary phase. Two strains were recovered by centrifugation, and then cell wall mannoproteins were suspended in a citric acid buffer (pH 7.0), followed by sterilization under high pressure (121° C., 1 hr). Then, ethanol was added thereto, and cell wall proteins were recovered by centrifugation. The recovered cell wall proteins were treated with a peptide-N-glycosidase F (PNGase-F) to cleave the oligosaccharides, and the oligosaccharides were isolated and purified using PGC (porous graphite column). Then, the oligosaccharides were labeled with a fluorescent compound, 2-aminopyridine (PA). An HPLC analysis was performed under the same conditions to compare the profile of the oligosaccharide between two strains. The HPLC analysis was performed using an amine column (Asahipak NH2P-504E, Showa denko, Japan), and a linear gradient of a solvent A (100% acetonitrile) and a solvent B (0.2 M triethylamine-acetic acid, pH 7.0) at a ratio of 60:40 to 25:75 and a flow rate of 1 ml/min for 60 min. The N-linked oligosaccharides labeled with a fluorescent compound (PA) were detected by fluorescence (excitation wavelength=315 nm and emission wavelength=380 nm).

As shown in FIGS. 8a and 8b, the profile of neutral sugar chain of Ylmpo1Δ strain exhibited the same pattern as that of wild-type. However, the profile of acidic sugar chain with mannosylphosphate (region marked with *) was not observed. The results indicate that the mannosylphosphorylation of N-linked oligosaccharides can be completely suppressed by a single disruption of YlMPO1 gene (SEQ ID NO: 1).

EXAMPLE 7

Alcain Blue Staining

A cationic phthalocyanine dye, alcian blue is characterized by binding to anionic cell surface, and the extent of alcian blue staining is correlated with the amount of mannosylphosphate attached to mannoprotein in cell wall. Therefore, the wild-type strain and Ylmpo1Δ strain (M4D3P1) were subjected to alcian blue staining, and compared to each other to determine the amount of mannosylphosphate exposed on the cell wall.

First, the strains were cultured in YPD media at 28° C. for 16 hrs, and grown to stationary phase. Then, the cells were recovered, and washed with a 0.02 N hydrochloric acid solution (pH 3.0). The cells were reacted with a 0.02 N hydrochloric acid solution containing 0.1% alcian blue (Sigma, USA) at room temperature for 30 min, and then washed with distilled water. The cells were transferred to 96-well tissue culture plates, and color difference was observed. As shown in FIG. 8c, it was found that the Ylmpo1Δ strain was not well stained with alcian blue, as compared to the wild-type. The result indicates that the mannosylphosphorylation of oligosaccharides of cell wall proteins of Ylmpo1Δ strain was suppressed.

Industrial Applicability

In the present invention, *Yarrowia lipolytica* was developed as a host system for producing therapeutic glycoproteins derived from human, thereby being used in medical field as a host system capable of producing therapeutic glycoproteins of high quality and yield.

The invention claimed is:

1. An isolated and purified polypeptide comprising the amino acid sequence of SEQ ID NO 2.

2. An isolated and purified nucleic acid molecule consisting of a sequence encoding the polypeptide of SEQ ID NO. 2.

3. A *Yarrowia lipolytica* mutant strain in which the YlMPO1 gene having a base sequence of SEQ ID NO. 1 is disrupted and that produces glycoproteins lacking mannosylphosphate.

4. The *Yarrowia lipolytica* mutant strain according to claim 3, which is identified by accession number: KCTC 11102BP.

5. The *Yarrowia lipolytica* mutant strain according to claim 3, wherein the YlOCH1 gene is further disrupted to eliminate yeast-specific glycosylation.

6. The *Yarrowia lipolytica* mutant strain according to claim 5, which is identified by accession number: KCTC 11026BP.

7. A method for producing glycoproteins lacking yeast specific-mannosylphosphate, wherein a nucleic acid molecule encoding a foreign protein is introduced into the mutant strain of one of claims 3 to 5.

* * * * *